US012697449B2

(12) United States Patent
Andersson et al.

(10) Patent No.: US 12,697,449 B2
(45) Date of Patent: Aug. 4, 2026

(54) LUNG RECRUITMENT IN MECHANICAL VENTILATION

(71) Applicant: MAQUET CRITICAL CARE AB, Solna (SE)

(72) Inventors: Mari Andersson, Bandhagen (SE); Leif Lychou, Sundbyberg (SE); Sigun Israelsson, Järfälla (SE)

(73) Assignee: Maquet Critical Care AB, Solna (SE)

( * ) Notice: Subject to any disclaimer, the term of this patent is extended or adjusted under 35 U.S.C. 154(b) by 607 days.

(21) Appl. No.: 17/250,048

(22) PCT Filed: Oct. 17, 2018

(86) PCT No.: PCT/SE2018/051057
§ 371 (c)(1),
(2) Date: Nov. 12, 2020

(87) PCT Pub. No.: WO2020/080984
PCT Pub. Date: Apr. 23, 2020

(65) Prior Publication Data
US 2021/0213221 A1     Jul. 15, 2021

(51) Int. Cl.
*A61M 16/00*          (2006.01)
*A61M 16/08*          (2006.01)

(52) U.S. Cl.
CPC ... *A61M 16/024* (2017.08); *A61M 2016/0027* (2013.01); *A61M 2016/003* (2013.01); *A61M 16/0051* (2013.01); *A61M 16/0833* (2014.02)

(58) Field of Classification Search
CPC .. A61M 16/021–026; A61M 2230/005; A61M 2205/502; A61M 2230/46; A61M 16/024;

A61M 16/0051; A61M 16/0833; A61M 16/12; A61M 16/00; A61M 2016/0027; A61M 2016/003;
(Continued)

(56) References Cited

U.S. PATENT DOCUMENTS

| | | | |
|---|---|---|---|
| 5,738,090 A | 4/1998 | Lachmann et al. | |
| 8,551,009 B2 | 10/2013 | Sinderby | |

(Continued)

FOREIGN PATENT DOCUMENTS

| | | | | |
|---|---|---|---|---|
| CN | 105413030 | 3/2016 | | |
| EP | 1579882 A1 * | 9/2005 | ............. | A61B 5/085 |
| WO | 2012/139159 A1 | 10/2012 | | |

*Primary Examiner* — Kendra D Carter
*Assistant Examiner* — Maap Ellabib
(74) *Attorney, Agent, or Firm* — Fay Kaplun & Marcin, LLP

(57)          ABSTRACT

A ventilation system includes a breathing apparatus which provides a mechanical ventilation to a patient. The breathing apparatus is configured to perform, at a first point in time, an automated full recruitment manoeuvre, FRM, comprising a recruitment phase and a PEEP titration phase, the FRM being performed based on preset FRM settings. The breathing apparatus is further configured to perform, at a second and later point in time, an automated quick recruitment manoeuvre, QRM, comprising a recruitment phase but no PEEP titration phase, the QRM being performed based on preset QRM settings. The breathing apparatus is configured to initiate at least one QRM setting based on at least one FRM setting used for the FRM manoeuvre, and/or a result of the FRM manoeuvre.

11 Claims, 8 Drawing Sheets

(58) Field of Classification Search
CPC .. A61M 2016/0039; A61M 2016/0042; A61M
2205/505; A61M 2205/18
See application file for complete search history.

(56) References Cited

U.S. PATENT DOCUMENTS

| | | | |
|---|---|---|---|
| 9,173,595 B2 | 11/2015 | Böhm et al. | |
| 2002/0193699 A1* | 12/2002 | Blomberg | A61M 16/024 |
| | | | 600/533 |
| 2007/0068528 A1 | 3/2007 | Bohm et al. | |
| 2009/0241957 A1 | 10/2009 | Baker, Jr. | |
| 2009/0241958 A1* | 10/2009 | Baker, Jr. | A61B 5/14542 |
| | | | 128/204.23 |
| 2010/0095964 A1 | 4/2010 | Tham et al. | |
| 2010/0275920 A1 | 11/2010 | Tham et al. | |
| 2011/0023880 A1* | 2/2011 | Thiessen | A61M 16/0051 |
| | | | 128/204.23 |
| 2011/0029910 A1* | 2/2011 | Thiessen | A61M 16/205 |
| | | | 715/780 |
| 2018/0344958 A1* | 12/2018 | Heinonen | A61M 16/01 |
| 2019/0125994 A1* | 5/2019 | Du | A61M 16/026 |

* cited by examiner

LUNG RECRUITMENT IN MECHANICAL VENTILATION

TECHNICAL FIELD

The present disclosure relates to the field of mechanical ventilation and, in particular, to a ventilation system, a method, and a computer program for lung recruitment in mechanically ventilated patients.

BACKGROUND

Lung recruitment manoeuvres (RM) have gained attention over the past years to overcome lung collapse (atelectasis) and improve lung function in order to decrease the risk of developing ventilator induced lung injury (VILI) in mechanically ventilated patients suffering from Acute Respiratory Distress Syndrome (ARDS).

A poorly aerated lung with areas of collapsed alveoli will lead to poor ventilation of the patient, requiring higher driving pressures and $FiO_2$ settings to get adequate oxygenation of the patient. The recurring opening and collapse of alveoli during these conditions contributes to the risk of exacerbated lung injury with an increased risk of prolonged hospitalisation and mortality.

By applying a lung protective strategy through re-recruiting collapsed lung tissue and applying an appropriate end-expiratory pressure (PEEP) in order to sustain an open lung, the lung function is improved and morbidity in mechanically ventilated patients may be substantially reduced.

The literature describes different types of lung recruitment manoeuvers, where the simplest ones include sustained inflation at a fixed pressure for a fixed time interval, e.g. 40 $cmH_2O$ for 40 seconds, or a slow gradual increase in airway pressure through a constant flow for a single inflation/deflation cycle. Another lung recruitment strategy that has been proved successful is a stepwise manoeuvre where PEEP and peak pressure is first increased over a number of breaths until a pressure plateau is maintained for up to two minutes, followed by a PEEP titration phase where an optimal PEEP is identified to achieve a volume target for the patient.

Such a stepwise lung recruitment manoeuvre is described in U.S. Pat. No. 9,173,595. According to the recruitment manoeuvre disclosed in U.S. Pat. No. 9,173,595, data samples of gas concentration of expired gas are used to calculate tracing values that are sensitive to changes of alveolar dead space, whereby the tracing values are used to determine an optimal PEEP during the PEEP titration phase.

Another stepwise and at least partly automated lung recruitment strategy is disclosed in WO 2012/139159. According to the recruitment strategy disclosed in WO 2012/139159, the compliance of the patient's respiratory system is analysed to find an optimal PEEP during the PEEP titration phase.

There are several challenges associated with automation of lung recruitment manoeuvres. Some challenges relate to the handling of the high and potentially harmful pressures and flows required for effective lung recruitment. Other challenges relate to the optimisation of ventilation settings during and after the lung recruitment manoeuvre. Yet other challenges relate to the complexity of configuration and initiation of the lung recruitment manoeuvre.

SUMMARY

It is an objective of the disclosure to present an automated lung recruitment manoeuvre that addresses one or more of the above mentioned challenges.

It is a particular objective of the disclosure to present an automated recruitment manoeuvre that can be quickly yet safely initiated by a clinician.

It is yet another objective of the disclosure to present an automated recruitment manoeuvre that minimises potentially adverse effects of the lung recruitment manoeuvre on the lungs of the ventilated patient.

These and other objectives are achieved in accordance with the present disclosure by a ventilation system, a method, and a computer program as defined by the appended claims.

According to an aspect of the disclosure, there is provided a ventilation system comprising a breathing apparatus for providing mechanical ventilation to a patient. The breathing apparatus is configured to perform, at a first point in time, an automated recruitment manoeuvre comprising at least a recruitment phase and a PEEP titration phase, herein referred to as a full recruitment manoeuvre, FRM. The FRM manoeuvre is performed based on preset FRM settings. The breathing apparatus is further configured to perform, at a second at later point in time, an automated recruitment manoeuvre comprising a recruitment phase but no PEEP titration phase, herein referred to as a quick recruitment manoeuvre, QRM. The QRM is performed based on preset QRM settings. The breathing apparatus is configured to initiate at least one QRM setting based on at least one FRM setting used for the FRM manoeuvre, and/or a result of the FRM manoeuvre.

An FRM manoeuvre is typically performed by a physician specifically trained in lung dynamics. In many cases, a lung sick patient in need of FRM will also require recurring suctioning of the airways to remove mucus. During suctioning, lung pressure is released and, as a result, collapse of alveoli will reoccur. To get back to optimal ventilation, the lung needs to be re-recruited before the ventilation will have the same effects as prior to the suctioning. Suctioning of a patient is typically a task of a nurse, which does not have the same skill level as the physician. The proposed ventilation system allows for nurses and other medical personnel not being specifically trained in lung dynamics to open up the alveoli of the patient using a QRM manoeuvre with settings inherited from a previously performed FRM manoeuvre. This could lead to improved patient care and increased patient safety.

In the workflow of the suction procedure re-recruitment through QRM or a reminder to perform a QRM could be included. The diagnostic step to decide whether or not a QRM is needed may also be included in the workflow. The breathing apparatus may, for example, be configured to compare parameters monitored prior and after suctioning, and to suggests a QRM to be performed if there are deviations. Dynamic compliance, oxygen saturation (e.g. SpO2) and tidal volume are examples of parameters that may be suitable for comparison. If a QRM is suggested, a short cut may appear on a graphical user interface of the breathing apparatus that directly "leads" the operator to the QRM manoeuvre with settings initiated from a previously performed FRM manoeuvre (if such a procedure has been performed).

In addition to suctioning, there are other reasons for and interactions with the patient that causes lung pressure to be released and collapse of alveoli to reoccur. Transport of the patient or that the patient moves or is moved when attended to are some examples of such interactions. Regardless of the reason to the collapse of alveoli, the breathing apparatus may be configured to suggest, for example through a smart prompt on the graphical user interface, a QRM after a specific procedure (such as suctioning exemplified above) or if a certain threshold of a parameter being indicative of collapse of alveoli or other has been reached. Non-limiting examples of such parameters are dynamic compliance, oxygen saturation (e.g. SpO2), tidal volume, FiO2 (fraction of inspired O2) and stress index. The breathing apparatus may be configured monitor and to compare at least one such parameter prior to a specific procedure (e.g. suctioning, transport) and after and if there are deviations suggest a QRM. Alternatively, the breathing apparatus may be configured to compare at least one such parameter to a predefined threshold value and when such a threshold value is reached or passed, suggest a QRM. Any level of such a threshold will be individually set based on patient condition, weight, height etc. If a QRM is suggested, a short cut may appear on a graphical user interface of the breathing apparatus that directly "leads" the operator to the QRM manoeuvre with settings initiated from settings and/or results of the previously performed FRM manoeuvre (if such a procedure has been performed). If a FRM manoeuvre has not previously been performed on the patient, the decision support prompt on the graphical user interface may recommend that a FRM manoeuvre should be performed and present a short cut to the FRM manoeuvre.

In addition, if a certain predefined time has elapsed since the last performed FRM or QRM, the decision support prompt on the graphical user interface may recommend a QRM and present a short cut to the QRM manoeuvre with settings initiated from settings and/or results of the previously performed FRM manoeuvre. The breathing apparatus may be configured to initiate the QRM without user acknowledgement if approved during set up of parameters for the recruitment procedure or monitoring and/or if the patient fulfils certain criteria e.g with respect to the lung status/condition of the patient.

Besides reducing the demand for clinical expertise by using settings and/or results from a previous FRM manoeuvre to initiate settings for the QRM manoeuvre, the QRM can be initiated quickly, with a minimum of manual input of information to the breathing apparatus. The non-requirement of manual input of QRM settings further improves safety of the QRM manoeuvre since the risk of human errors is minimised.

The breathing apparatus may be configured to initiate the at least one QRM setting based on the FRM settings used for the FRM manoeuvre. For example, the breathing apparatus may set an initial value for the at least one QRM setting that is substantially equal to a value of a corresponding FRM setting, used for the FRM manoeuvre. Besides minimising the time required for manual input of information, this has the further effect that a breathing apparatus operator knowing that the settings for the QRM manoeuvre are initiated based on the settings of the previously performed (and approved) FRM manoeuvre does not have to spend the same amount of time on ensuring that the automatically initiated settings are correct, as normally would have been required if the automatically initiated settings were default settings generated based on, e.g., a patient category.

The breathing apparatus may also be configured to initiate the at least one QRM setting based on a result of the FRM manoeuvre. An effect of setting the at least one QRM setting based on the result of the FRM manoeuvre is that the lung dynamics of the patient, as reflected by the result of the FRM manoeuvre, can be taken into account in the initiation of QRM settings. That the at least one QRM setting is initiated based on a result of the FRM manoeuvre herein means that the QRM setting is initiated based on at least one parameter determined during the FRM manoeuvre. Typically but not necessarily, the parameter is a physiological parameter relating to the lung dynamics of the ventilated patient.

For example, the at least one QRM setting that is initiated based on a result of the FRM manoeuvre may comprise a PEEP setting to be used during a period of post-recruitment manoeuvre (post-RM) ventilation following the QRM manoeuvre, which PEEP setting is initiated based on an optimal PEEP of the ventilated patient determined by the breathing apparatus during the FRM manoeuvre. In this way, knowledge on the lung dynamics of the patient, obtained e.g. during a PEEP titration phase of the previous FRM manoeuvre, may be used in a subsequent QRM manoeuvre to ensure that the PEEP level set for the post-RM period is well-adapted to the lung dynamics of the patient.

In another example, the at least one QRM setting that is initiated based on a result of the FRM manoeuvre may comprise a maximum peak inspiratory pressure (PIP) and/or a maximum PEEP setting to be used during the recruitment phase of the QRM manoeuvre, which maximum PIP setting and/or maximum PEEP setting is initiated from an optimal PEEP and/or an alveolar opening pressure of the patient (3), determined during the FRM manoeuvre.

Preferably, the breathing apparatus is configured to initiate at least one QRM setting based on (e.g. substantially equal to) a corresponding FRM setting used for the FRM manoeuvre, and to initiate at least one other QRM setting based on the result of the FRM manoeuvre. In this way, at least one QRM setting can be initiated to make the QRM manoeuvre resemble the FRM manoeuvre, e.g. in terms of pressure trajectories applied to the patient, while the at least one other QRM setting can be initiated based on an assumed result of the QMR manoeuvre, which, due to the similar settings for the QRM and FRM manoeuvre, can be assumed to correspond to the result of the FRM manoeuvre.

For example, the breathing apparatus may be configured to set initial values for QRM settings defining a PIP trajectory and a PEEP trajectory of the QRM manoeuvre based on (e.g. substantially equal to) corresponding FRM settings for defining a PIP trajectory and a PEEP trajectory of the FRM manoeuvre, and to set an initial value for the post-QRM PEEP setting based on the optimal PEEP determined during the PEEP titration phase of the FRM manoeuvre.

In another example, the breathing apparatus may be configured to set initial values for QRM settings defining an incremental limb of a PIP trajectory and a PEEP trajectory of the QRM manoeuvre at least substantially equal to corresponding FRM settings for defining an incremental limb of a PIP trajectory and a PEEP trajectory of the FRM manoeuvre, and to set an initial value for a maximum PIP setting defining a maximum PIP of the PIP trajectory of the QRM manoeuvre based on an alveolar opening pressure determined during the recruitment phase of the FRM manoeuvre.

The breathing apparatus may further be configured to initiate the at least one QRM setting from the settings and/or the result of a previously performed FRM manoeuvre only if the FRM and QRM manoeuvres are performed for the same patient, and only if the previous FRM manoeuvre was performed within a predefined time from initiation of the QRM settings. To this end, the breathing apparatus may be configured to determine a time elapsed since the FRM manoeuvre was performed, and to initiate the at least one QRM setting from settings and/or results of the FRM manoeuvre only if the time elapsed is less than a predefined threshold value. This has the effect of minimising the risk of substantial changes in lung dynamics of the patient between an FRM manoeuvre and a QRM manoeuvre performed based on QRM settings initiated from the FRM manoeuvre. The threshold value may for instance be set to 24 hours. In one exemplary embodiment, the breathing apparatus may be configured to prompt the operator to select whether QRM settings should be initiated from the previously performed FRM manoeuvre or from default settings if the threshold value is exceeded when the QRM manoeuvre is to be performed.

According to another example, the breathing apparatus may be configured to analyse a trend for one or more respiratory parameters after the FRM was performed, and to initiate QRM settings based on the FRM only if the trend indicates that no substantial changes in lung dynamics of the ventilated patient has occurred since the FRM manoeuvre.

It should also be noted that there is often a need for repeated QRMs for critically ill patients, and that QRM settings for one or more QRMs may be initiated from the same FRM.

The at least one QRM setting may be any of, or any combination of:

a PEEP max setting for setting a maximum PEEP for the QRM recruitment phase, which PEEP max setting is initiated from any of, or any combination of, a corresponding PEEP max setting set for the FRM manoeuvre, an alveolar opening pressure determined during the FRM manoeuvre, and an optimal PEEP determined during the FRM manoeuvre;

a PIP max setting for setting a maximum PIP for the QRM recruitment phase, which PIP max setting is initiated from any of, or any combination of, a corresponding PIP max setting set for the FRM manoeuvre, an alveolar opening pressure determined during the FRM manoeuvre, and an optimal PEEP determined during the FRM manoeuvre;

a PEEP incr/step setting for setting an incremental increase in PEEP between consecutive PEEP steps of the QRM recruitment phase, which PEEP incr/step setting is initiated from a corresponding PEEP incr/step setting set for the FRM manoeuvre;

a Recruitment rate setting for setting a respiratory rate for the QRM recruitment phase, which Recruitment rate setting is initiated from a corresponding Recruitment rate setting set for the FRM manoeuvre;

a Breaths/step setting for setting a number of breaths on each PEEP step of the QRM recruitment phase, which Breaths/step setting is initiated from a corresponding Breaths/step setting set for the FRM manoeuvre;

a Breaths at PEEP max setting for setting a number of breaths at the maximum PEEP level of the QRM recruitment phase, which Breaths at PEEP max setting is initiated from a corresponding Breaths at PEEP max setting set for the FRM manoeuvre;

an I:E ratio for setting an inspiration-to-expiration ratio for breaths of the QRM recruitment phase, which I:E ratio is initiated from a corresponding I:E ratio setting set for the FRM manoeuvre, an inspiratory time setting for setting an inspiratory time for breaths of the QRM recruitment phase, which inspiratory time setting is initiated from a corresponding inspiratory time setting for the FRM manoeuvre, and a Post-RM PEEP setting for setting a PEEP for a period of post-RM ventilation following the QRM manoeuvre.

Typically, one or more of the PEEP incr/step, Recruitment rate, Breaths/step and Breaths at PEEP max settings are initiated from corresponding FRM settings for the FRM manoeuvre. Preferably, they are all initiated from corresponding FRM settings.

Typically, at least the Post-RM PEEP setting is initiated from a result of the FRM manoeuvre. As mentioned above, the Post-RM PEEP setting may for instance be initiated based on an optimal PEEP determined by the breathing apparatus during the PEEP titration phase of the FRM manoeuvre.

The PEEP max and/or PIP max settings may, in some embodiments, be initiated from corresponding FRM settings for the FRM manoeuvre. In other embodiments, however, the PEEP max and/or PIP max settings may be initiated from a result of the FRM manoeuvre. As mentioned above, PEEP max and/or PIP max may for instance be initiated based on the optimal PEEP determined by the breathing apparatus during the PEEP titration phase of the FRM manoeuvre, or based on an alveolar opening pressure of the ventilated patient, as determined by the breathing apparatus during the FRM recruitment phase.

According to another aspect of the present disclosure, there is provided a method for lung recruitment in a mechanically ventilated patient. The method comprises the steps of:

performing, at a first point in time, an FRM comprising a recruitment phase and a PEEP titration phase, the FRM being performed based on preset FRM settings, and performing, at a second and later point in time, a QRM comprising a recruitment phase but no PEEP titration phase, the QRM being performed based on preset QRM settings, wherein at least one of the QRM settings is initiated based on at least one FRM setting used for the FRM manoeuvre, and/or a result of the FRM manoeuvre.

Typically, at least one QRM setting is initiated based on a result of the FRM manoeuvre. The at least one QRM setting that is initiated from a result of the FRM manoeuvre may be any or both of a PEEP setting to be used during a period of post-RM ventilation following the QRM manoeuvre and a maximum PIP and/or PEEP setting to be used during the recruitment phase of the QRM procedure. The PEEP setting may, for instance, be initiated based on an optimal PEEP determined during the PEEP titration phase of the FRM manoeuvre, whereas the maximum PIP and/or PEEP may be initiated based on the optimal PEEP and/or an alveolar opening pressure of the patient, determined during the recruitment phase of the FRM manoeuvre.

Typically, at least one other QRM setting is initiated based on a corresponding FRM setting used for the FRM manoeuvre. The at least one QRM setting that is initiated based on a corresponding FRM setting may comprise QRM recruitment settings defining pressure trajectories for PIP and PEEP to be followed during the QRM recruitment phase, which QRM recruitment settings are initiated based on corresponding FRM settings defining pressure trajectories for PIP and PEEP used for the FRM manoeuvre.

The method may further comprise a step of determining a time elapsed since the FRM manoeuvre was performed, whereby the at least one QRM setting may be initiated from settings and/or results of the FRM manoeuvre only if the time elapsed is less than a predefined threshold value.

The method is typically a computer-implemented method performed at least in parts by the breathing apparatus upon execution of a computer program by a breathing apparatus computer. Consequently, according to another aspect of the present disclosure, there is provided a computer program for lung recruitment in a mechanically ventilated patient. The computer program comprises computer-readable instructions which, when executed by a computer a ventilation system comprising a breathing apparatus, causes the ventilation system to perform any of, or any combination of, the above described method steps.

The computer program may be stored in a non-volatile memory of the ventilation system, e.g. in a non-volatile memory hardware device of the breathing apparatus.

The proposed method may be performed using standard hardware of a state-of-the-art breathing apparatus. Consequently, installation of the computer program on existing breathing apparatuses may allow existing breathing apparatuses to perform the proposed method without hardware modification.

More advantageous aspects of the proposed ventilation system, method and computer program will be described in the detailed description of embodiments following hereinafter.

Advantages similar to the above mentioned advantages may also be obtained by initiating FRM settings for an FRM manoeuvre based on FRM settings and/or a result of a previously performed FRM manoeuvre. Consequently, according to another aspect of the disclosure, there is provided a ventilation system comprising a breathing apparatus for providing mechanical ventilation to a patient. The breathing apparatus is configured to perform, at a first point in time, a first FRM manoeuvre comprising at least a recruitment phase and a PEEP titration phase. The first FRM manoeuvre is performed based on a first set of preset FRM settings. The breathing apparatus is further configured to perform, at a second at later point in time, a second FRM manoeuvre comprising at least a recruitment phase and a PEEP titration phase. The second FRM manoeuvre is performed based on a second set of preset FRM settings. The breathing apparatus is configured to initiate at least one of the FRM settings of the second FRM manoeuvre based on at least one FRM setting used for the first FRM manoeuvre, and/or a result of the first FRM manoeuvre. This has the advantage of minimising manual workload and the time required to initiate an FRM manoeuvre following a previously performed FRM manoeuvre. It further has the effect of allowing the settings of the second FRM manoeuvre to be adapted to the lung dynamics of the patient, as determined by the breathing apparatus during the previous FRM manoeuvre.

Preferably, at least one of the FRM settings of the second FRM manoeuvre is initiated based on the result of the first manoeuvre, meaning that the at least one FRM setting of the second FRM manoeuvre is initiated based on at least one parameter determined during the first FRM manoeuvre.

For example, the PIP max and/or PEEP max setting of the second FRM manoeuvre may be initiated based on the optimal PEEP of the ventilated patient, determined during the first FRM manoeuvre. Also the settings for start and minimum PEEP levels of the PEEP titration phase of the second FRM may be initiated based on the optimal PEEP determined during the first FRM manoeuvre.

Typically, for reasons mentioned above in relation to initiation of QRM settings from FRM settings, some of the FRM settings for the second FRM manoeuvre are initiated based on corresponding settings used for the first FRM manoeuvre, whereas other FRM settings of the second FRM manoeuvre are initiated based on the results of the first FRM manoeuvre.

Some of the above mentioned advantages may also be obtained by initiating FRM settings for an FRM manoeuvre based on QRM settings of a previously performed QRM manoeuvre. Consequently, according to another aspect of the disclosure, there is provided a ventilation system comprising a breathing apparatus for providing mechanical ventilation to a patient. The breathing apparatus is configured to perform, at a first point in time, an automated recruitment manoeuvre comprising at least a recruitment phase and a PEEP titration phase, herein referred to as a full recruitment manoeuvre, FRM. The FRM manoeuvre is performed based on preset FRM settings. The breathing apparatus is further configured to perform, at a first point in time, a QRM manoeuvre comprising a recruitment phase. The QRM manoeuvre is performed based on preset QRM settings. The breathing apparatus is further configured to perform, at a second at later point in time, an FRM manoeuvre comprising at least a recruitment phase and a PEEP titration phase. The FRM manoeuvre is performed based on preset FRM settings. The breathing apparatus is configured to initiate at least one of the FRM settings of the FRM manoeuvre based on at least one QRM setting used for the QRM manoeuvre. This has the advantage of minimising manual workload and the time required to initiate an FRM manoeuvre following a QRM manoeuvre.

BRIEF DESCRIPTION OF THE DRAWINGS

The present invention will become more fully understood from the detailed description provided hereinafter and the accompanying drawings which are given by way of illustration only. In the different drawings, same reference numerals correspond to the same element.

DETAILED DESCRIPTION

The present disclosure relates to an automated lung recruitment manoeuvre for re-opening collapsed alveoli in a mechanically ventilated patient. The recruitment manoeuvre may be automatically performed by a breathing apparatus providing the mechanical ventilation to the patient. The recruitment manoeuvre may be fully implemented in software, thus allowing a conventionally equipped breathing apparatus to perform the manoeuvre with no modification of existing hardware.

Figure 1:
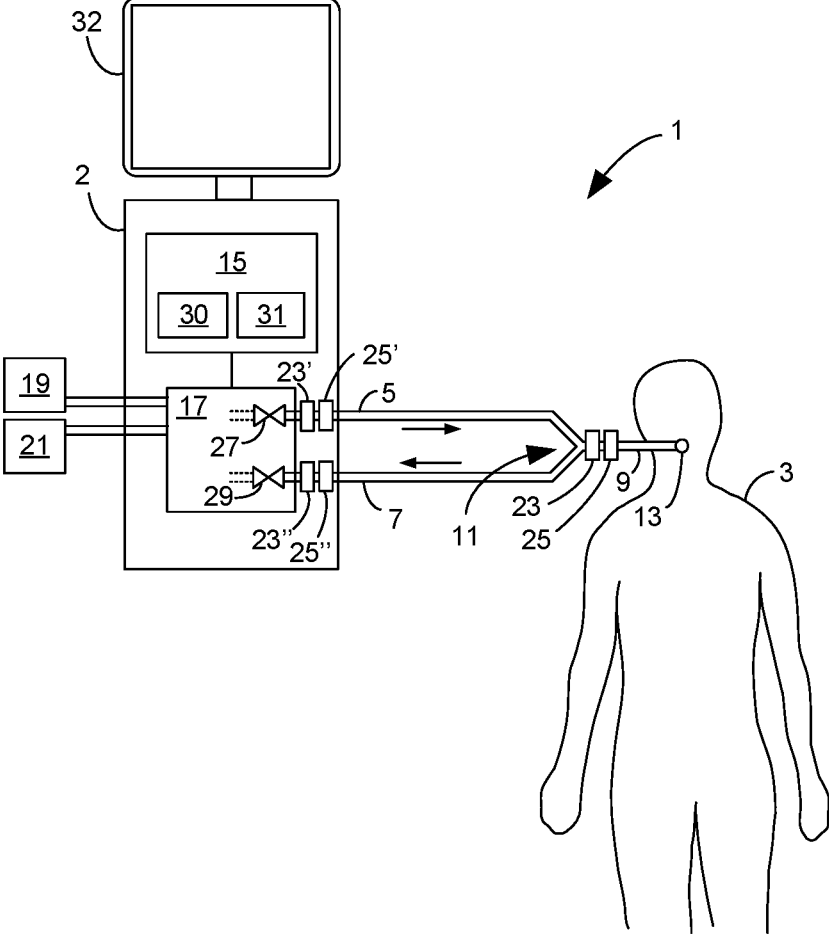
FIG. 1 illustrates an exemplary embodiment of a mechanical ventilation system for performing an automated recruitment manoeuvre in accordance with an exemplary embodiment of the disclosure.

FIG. 1 illustrates an exemplary embodiment of a mechanical ventilation system 1 comprising a breathing apparatus 2 configured to perform an automated recruitment manoeuvre in accordance with the principles disclosed herein. The breathing apparatus 2 may be any type of apparatus capable of providing mechanical ventilation to the patient 3 through the supply of pressurised breathing gas to the airways of the patient 3. Ventilators and anaesthesia machines are non-limiting examples of such breathing apparatuses.

The breathing apparatus 2 is connected to the patient 3 via a patient circuit comprising an inspiratory line 5 for supplying breathing gas to the patient 3, and an expiratory line 7 for conveying expiration gas away from the patient 3. The inspiratory line 5 and the expiratory line 7 are connected to to the patient 3 via a patient connector 13, such as an endotracheal tube. The inspiratory line 5 and the expiratory line 7 may be connected to the patient connector either directly (if using double lumen tubing) or via a Y-piece. In the illustrated example, the inspiratory line 5 and the expiratory line 7 are connected to a common line 9 via a Y-piece 11, which common line is connected to the patient 3 via the patient connector 13.

The breathing apparatus 2 comprises a control unit or control computer 15 for controlling the ventilation of the patient 3 based on pre-set parameters and/or measurements obtained by various sensors of the breathing apparatus. The control computer 15 controls the ventilation of the patient 3 by controlling a pneumatic unit 17 of the breathing apparatus 2, which pneumatic unit 17 is connected on one hand to one or more gas sources 19, 21 and on the other hand to the inspiratory line 5 for regulating a flow and/or pressure of breathing gas delivered to the patient 3. The pneumatic unit 17 may comprise various gas mixing and regulating means well known in the art of ventilation, such as gas mixing chambers, controllable gas mixing valves, turbines, controllable inspiration and/or expiration valves, etc.

The ventilation system 1 further comprises one or more flow sensors 23, 23', 23" for measuring respiratory flow, and one or more pressure sensors 25, 25', 25" for measuring respiratory pressure. The flow sensor 23 may be a proximal flow sensor located close to the patient 3 (e.g. in or close to the Y-piece 11) and configured to measure both an inspiratory flow of breathing gas delivered towards the patient 3 during inspiration, and an expiratory flow of gas exhaled by the patient 3 during expiration. Likewise, the pressure sensor 25 may be a proximal pressure sensor located close to the patient 3 (e.g. in or close to the Y-piece 11) and configured to measure, during both inspiration and expiration, a proximate patient pressure substantially corresponding to an airway pressure of the patient 3. Alternatively or in addition to the flow sensor 23 and the pressure sensor 25 disposed in the Y-piece 11 of the patient circuit, the breathing apparatus 2 may comprise one or more internal flow sensors for measuring respiratory gas flow, and/or one or more internal pressure sensors for measuring respiratory gas pressure. For example, the breathing apparatus 2 may comprise a flow sensor 23' for measuring a flow of breathing gas in an inspiratory flow channel of the breathing apparatus 2, and/or a pressure sensor 25' for measuring a gas pressure in the inspiratory flow channel of the breathing apparatus. Alternatively, or in addition, the breathing apparatus 2 may comprise a flow sensor 23" for measuring a flow of expiration gas in an expiratory flow channel of the breathing apparatus 2, and/or a pressure sensor 25" for measuring a gas pressure in the expiratory flow channel of the breathing apparatus.

The measurement signals obtained by the one or more flow sensors 23, 23', 23" and the one or more pressure sensors 25, 25', 25" are transmitted to the control computer 15, whereby the control computer 15 can control the flow and volume of breathing gas delivered to the patient 3, as well as the airway pressure of the patient 3, by controlling the pneumatic unit 17 based on the measurement signals. In this exemplary embodiment, the pneumatic unit 17 comprises a controllable inspiratory valve 27 for regulating inspiratory flow and pressure, and a controllable expiratory valve 29 for controlling an expiratory pressure applied to the patient 3 during expiration.

The control computer 15 comprises a processor or processing unit 30 and a non-volatile memory hardware device 31 storing one or more computer programs for controlling the operation of the breathing apparatus 2, including a computer program for lung recruitment comprising instructions for carrying out an automated lung recruitment manoeuvre in accordance with the principles described herein. Unless stated otherwise, actions and method steps described hereinafter are performed by, or caused by, the control computer 15 of the breathing apparatus 2 upon execution by the processing unit 30 of different code segments of the computer program for lung recruitment, stored in the memory 31. The computer program further comprises functionality for configuring, initiating, monitoring and evaluating the automated lung recruitment manoeuvre. This functionality will hereinafter be referred to as the Open Lung Tool (OLT) of the breathing apparatus 3.

The automated lung recruitment manoeuvre and the OLT tool of the breathing apparatus 2 will now be described with reference made to FIGS. 1-8.

In general, in order to ensure sufficient gas exchange within the lungs of the patient 3, the tidal volume must be sufficiently large. The tidal volume of the ventilated patient depends on the pressure applied to the airways of the patient and the compliance of the patient's lungs. Therefore, a certain pressure swing between a pressure applied to the patient at the start of inspiration (typically corresponding to a positive end-expiratory pressure, PEEP, of the preceding expiration) and a peak inspiratory pressure, PIP, (in many cases corresponding to an end-inspiratory pressure, EIP), is required in order to achieve a sufficient tidal volume. Besides re-opening of collapsed alveoli, the aim of the lung recruitment manoeuvre is to find a setting for PEEP which is high enough to prevent re-collapse of recruited alveoli while being low enough to allow for sufficient tidal volumes at relatively low inspiratory peak pressures.

Figures 2, 3:
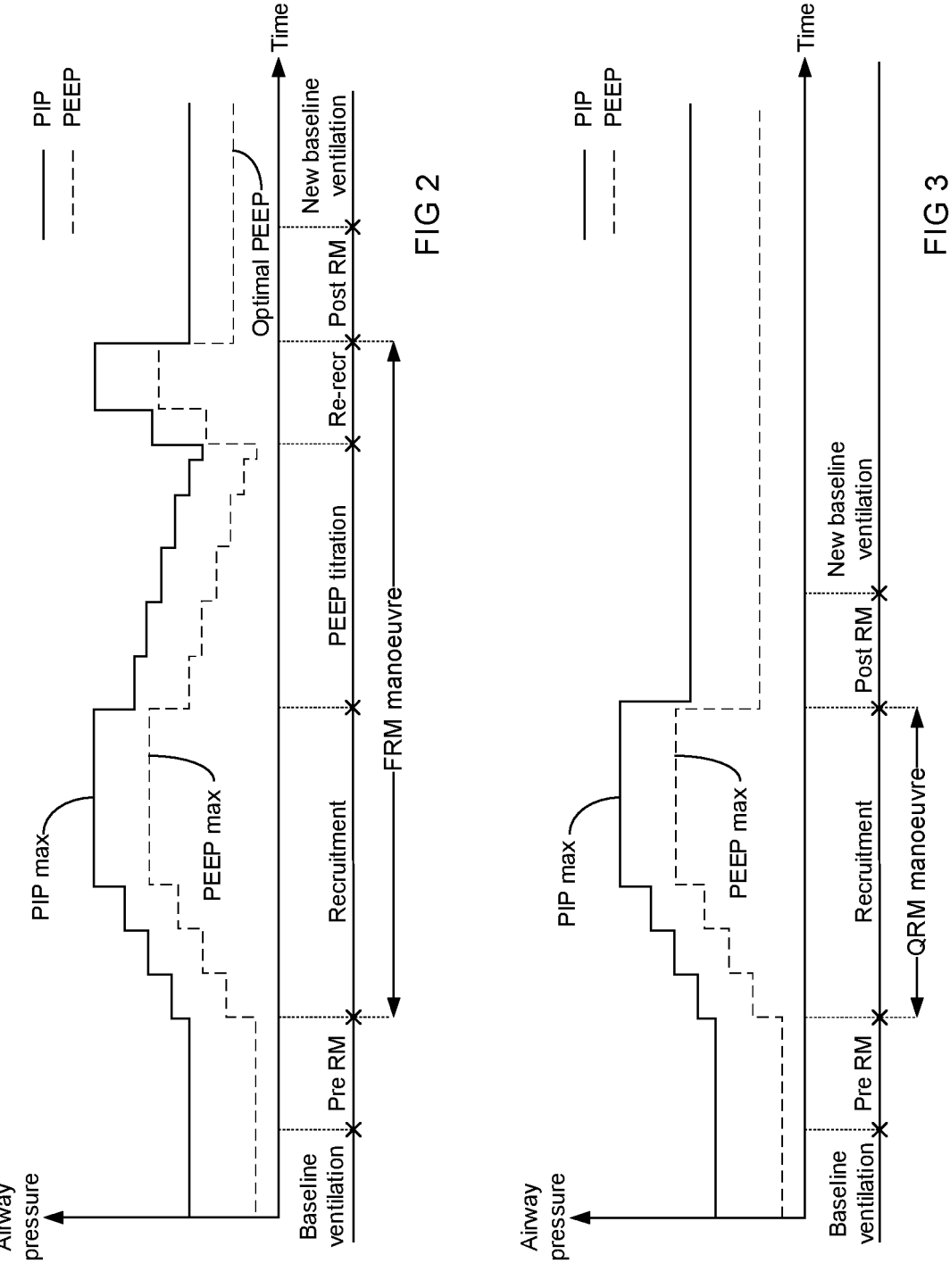
FIG. 2 illustrates pressure trajectories for PEEP and PIP during a full recruitment manoeuvre, FRM.
FIG. 3 illustrates pressure trajectories for PEEP and PIP during a quick recruitment manoeuvre, QRM.

Reference will now be made to FIGS. 2 and 3, illustrating exemplary embodiments of two different types of lung recruitment manoeuvres that may be automatically performed by the breathing apparatus 2 in FIG. 1.

FIG. 2 illustrates a full recruitment manoeuvre (FRM) comprising a recruitment phase, a PEEP titration phase and an optional re-recruitment phase following the PEEP titration phase. An FRM is typically performed when the patient 3 has not been subjected to any previous lung recruitment manoeuvre and there is no previous knowledge on the lung dynamics of the patient, or when there is reasons to believe that the lung dynamics of the patient have changed since a previously performed FRM, e.g. after changes in the position or the overall physiological state of the patient.

FIG. 3 illustrates a quick recruitment phase (QRM) comprising a recruitment phase without subsequent PEEP titration or re-recruitment phases. A QRM may be advantageously performed in situations where the optimal PEEP level is known beforehand (e.g. from a previous FRM) and where substantial changes in the lung dynamics of the patient is not anticipated. The primary intention with the QRM manoeuvre is to provide a standardised and safe way of recruiting alveoli that have collapsed due to temporary disconnection of the patient 3 from the breathing apparatus 2, e.g. after patient transportation or suctioning procedures. QRM may also be advantageously used instead of FRM for healthy patients not suffering from severe lung injuries, where a perfect adaption of ventilator settings to the lung dynamics of the patient is less crucial.

The recruitment phase of both the FRM and QRM manoeuvres involves an increase in one or both of PIP and PEEP in order to open up closed alveoli. The increase may be a single-step increase in PIP and/or PEEP but, more commonly, the increase is a gradual increase in PIP and/or PEEP that is performed to gradually prepare the lungs for the relatively high plateau pressures often required to open up closed alveoli. In the illustrated embodiments, the recruitment phase of both the FRM manoeuvre and the QRM manoeuvre is a phase of stepwise increase in both PEEP and PIP, from a respective minimum level to a respective maximum level.

The PEEP titration phase of the FRM manoeuvre is a phase of gradual decrease in PEEP for identifying a PEEP level that is optimised to the lung dynamics of the patient following the recruitment phase. This PEEP level is herein referred to as optimal PEEP. Typically, the PEEP titration phase is a phase of stepwise decrease in both PEEP and PIP, from a respective maximum level to a respective minimum level.

The purpose of the re-recruitment phase of the FRM manoeuvre is to re-open any alveoli collapsing during the PEEP titration phase, and in particular during the last steps of the PEEP titration phase. Like the recruitment phase, the re-recruitment phase of the FRM manoeuvre involves an increase in one or both of PIP and PEEP in order to open up closed alveoli. The increase may be a single-step increase in PIP and/or PEEP but, more commonly, the increase is a gradual increase in PIP and/or PEEP that is performed to gradually prepare the lungs for the relatively high plateau pressures often required to open up closed alveoli. In the illustrated embodiment, the re-recruitment phase of the FRM manoeuvre is a phase of stepwise increase in both PEEP and PIP, from a respective minimum level to a respective maximum level. Typically but not necessarily, the number of breaths on each step of the re-recruitment staircase and/or the number of steps in the re-recruitment staircase is reduced in relation to the recruitment staircase.

Prior to performing any of the FRM or the QRM manoeuvres, the patient is subject to baseline ventilation using baseline ventilation settings. The baseline ventilation may be any type of ventilation and take many different forms but is typically performed in a controlled mode of ventilation. The phase of baseline ventilation may be succeeded by an optional pre-recruitment (pre-RM) phase immediately preceding the recruitment manoeuvre. The purpose of the pre-RM phase is to collect comparison data to be used for evaluation of the recruitment manoeuvre through comparison with data collected during an optional post-recruitment (post-RM) phase following the recruitment manoeuvre. In the post-RM phase, the patient is ventilated with ventilation settings that at least to some extent are optimised to the changed lung dynamics of the patient, caused by the recruitment manoeuvre. As mentioned above, the post-RM phase further involves collection of post-RM comparison data, which post-RM comparison data is compared with the pre-RM comparison data to evaluate the effect on the patient of the post-RM ventilation with optimised ventilation settings. Evaluation data indicative of the effect on the patient may be presented to the operator in the post-RM phase, together with the optimised ventilation settings used during the post-RM phase and suggested for use during new baseline ventilation following the post-RM phase. If the operator acknowledges the suggested ventilation settings, the patient will be subject to new baseline ventilation using the optimised ventilation settings. In this case, the FRM and QRM manoeuvres can be said to constitute semi-automated manoeuvres only requiring the operator to acknowledge use of suggested ventilation settings for new baseline ventilation. In alternative embodiments, the breathing apparatus 2 performing the FRM or QRM manoeuvre may be configured to automatically enter into new baseline ventilation with optimised ventilation settings following the manoeuvre, in which case the manoeuvre can be said to be fully automated.

The Full Recruitment Manoeuvre-FRM

The exemplary FRM manoeuvre illustrated in FIG. 2 will now be described in more detail with reference to FIGS. 4-6. The FRM manoeuvre and the procedure for carrying out an FRM manoeuvre may include the following phases:

1) A planning phase for planning the FRM manoeuvre by selecting recruitment and PEEP titration settings;

2) A pre-RM phase involving collection of: comparison data indicative of the situation prior to FRM;

3) A recruitment phase for opening up collapsed alveoli, comprising a. a recruitment pre-conditioning phase of stepwise increase of PEEP and PIP to prepare lung for recruitment, and b. a plateau recruitment phase involving a potentially prolonged last step of the recruitment staircase;

4) A PEEP titration phase involving identification of a an optimal PEEP of the patient;

5) A re-recruitment phase that is similar to the FRM recruitment phase but typically shorter in duration, and 6) A post-RM phase involving ventilation with optimised ventilation settings, including optimised PEEP determined during the PEEP titration phase, with initial collection of comparison data for comparison with pre-RM comparison data.

FRM: Planning Phase

The above mentioned OLT tool of the breathing apparatus 2 comprises a user interface, e.g. a graphical user interface presented on a display 32 of the breathing apparatus 2 (see FIG. 1), through which a breathing apparatus operator may plan, initiate, monitor and evaluate the FRM and QRM manoeuvres, as further described below. Via the OLT interface, the breathing apparatus operator may enter planning views with relevant settings for configuring the FRM and QRM manoeuvres. An exemplary FRM planning view 33 comprising user-adjustable FRM settings for configuring the FRM manoeuvre is illustrated in FIG. 4. That a setting is user-adjustable herein means that it may be modified by a user.

The FRM settings include settings for maximum PEEP (PEEP max), maximum PIP (PIP max), incremental increase in PEEP (PEEP incr/step), respiratory rate (Recruitment rate), breaths per PEEP step during recruitment (Breaths/step), breaths at maximum PEEP (Breaths at PEEP max), starting PEEP for PEEP titration (PEEP start), tidal volume (VT/PBW) during PEEP titration, and breaths per PEEP step during PEEP titration (Breaths/step). When not preceded by a previous FRM manoeuvre, the FRM settings are typically default settings initiated for the relevant patient category (e.g. based on bodyweight). If, however, an FRM or a QRM manoeuvre has previously been performed for the same patient 3, the FRM settings may be initiated from the FRM or QRM settings used for the previous FRM or QRM manoeuvre. That a setting is initiated from another parameter (e.g. another setting), or initiated based on the other parameter, herein means that the setting is either set to a fixed and non-adjustable value, or that the setting (in case of a user-adjustable setting) is set to an initial value that can be adjusted by the user, which value is determined based on the other parameter.

Figure 4:
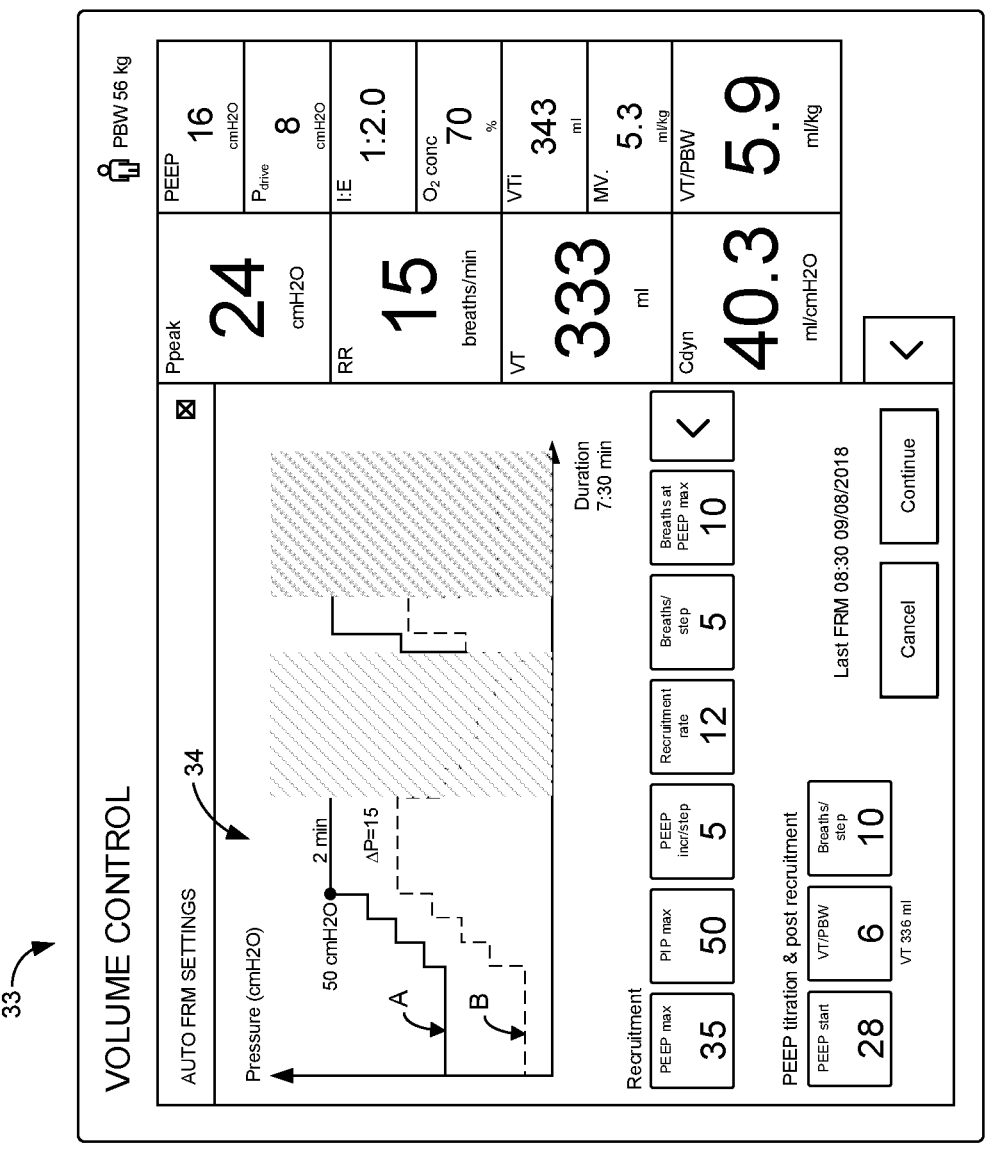
FIG. 4 illustrates an exemplary GUI view for planning an automated FRM manoeuvre.

As illustrated in FIG. 4, the FRM planning view 33 further comprises a visualisation 34 of the planned pressure trajectories for the FRM manoeuvre with clear indications of important characteristics of the manoeuvre, such as manoeuvre duration and PEEP and inspiratory peak pressure levels. Should the breathing apparatus operator change any FRM setting in the FRM planning view, the pressure trajectories of the visualisation 34 are updated accordingly. In the pressure trajectory visualisation, the planned PIP trajectory is denoted by reference sign A and the planned PEEP trajectory is denoted by reference sign B.

FRM: Pre-RM Phase

With reference again made to FIG. 2, prior to the pre-RM phase, the patient receives baseline ventilation in a preferred ventilation mode using preferred ventilation settings. Lung recruitment manoeuvres, including the proposed FRM and QRM manoeuvres, may cause severe discomfort to the patient and any spontaneous breathing efforts may prevent the manoeuvres from being performed in a safe and reliable manner. Therefore, FRM and QRM should be carried out in controlled modes of ventilation for patients having no or a minimum of spontaneous breathing. The baseline ventilation preceding the recruitment manoeuvre is therefore typically also performed in a controlled mode of ventilation, such as a pressure-controlled (PC) mode or a volume-controlled (VC) mode.

Upon initiation of the FRM manoeuvre, e.g. by actuation of a button by the operator, the breathing apparatus 2 enters the pre-RM phase in which the patient 3 is ventilated for a few breaths (typically around five breaths) using the ventilation mode and ventilation settings of the baseline ventilation. During this period of the pre-RM phase, hereinafter referred to as the pre-RM data collection period, comparison data to be compared with comparison data obtained after the recruitment manoeuvre is collected. As will be discussed later on, the collected data may for instance include information regarding a driving pressure (Pdrive) applied to the patient 3, a dynamic compliance (Cdyn) of the lungs of the patient, PEEP, PIP and the inspiratory tidal volume (VTi) of the patient.

The pre-RM data collection period is followed by a pre-RM PC period comprising a few breaths (typically around three) of baseline ventilation in PC mode, meaning that the breathing apparatus 2 may have to switch to PC mode if operated in any other controlled mode of ventilation during the baseline ventilation and the pre-RM data collection period. If so, the breathing apparatus 2 may be configured to automatically set a driving pressure for the pre-RM PC period resulting in a tidal volume corresponding to the tidal volume of the patient prior to switching to PC mode. The respiratory rate during the period of PC ventilation may be set to correspond to a respiratory rate setting (Recruitment rate) in the FRM planning view 33, the inspiration-to-expiration ratio (I:E) may be set to 1:1, and any trigger conditions for the triggering of additional breaths in response to spontaneous breathing efforts may be deactivated. For example, the conventional pressure trigger condition for PC mode may be deactivated by reducing the trigger sensitivity, e.g. by setting the trigger level to −20 cmH20. This level of PC ventilation constitutes a base level of the FRM recruitment staircase.

Furthermore, in the pre-RM phase, the breathing apparatus 2 automatically changes relevant alarm limits while other alarms may be pre-muted for the duration of the FRM manoeuvre. For example, the breathing apparatus may be configured to auto-adjust alarm limits for maximum PEEP and maximum PIP based on the FRM settings PEEP max and PIP max in the FRM planning view 33, and to pre-mute any alarm relating to minute ventilation and/or CO2 levels. Other alarms, such as an alarm for low PEEP, may also be changed or muted for the duration of the manoeuvre, or parts of the manoeuvre.

FRM: Recruitment Phase

During the recruitment phase of the FRM manoeuvre, PEEP and PIP are stepwise (incrementally) increased up to a respective plateau pressure corresponding to maximum PEEP and maximum PIP, as illustrated both in FIG. 2 and the visualisation 34 of the pressure trajectories in FIG. 4. In the illustrated example, although not required, changes in PEEP and PIP are made simultaneously. The size of each PEEP step, i.e. the incremental increase in PEEP, is determined by the step size setting (PEEP incr/step) in the FRM planning view 33. The size of each PIP step is determined by the maximum PIP setting (PIP max) and the number of steps in the recruitment staircase (as determined by an initial value for PEEP, the PEEP max setting and the PEEP incr/step setting). The incremental increase in PEEP for each step may, for instance, be in the range of 3-7 cmH2O. The number of breaths on each step of the recruitment staircase (i.e. on each PEEP level below maximum PEEP) and the number of breaths on the plateau (i.e. on the maximum PEEP level) are also determined by a respective setting (Breaths/step and Breaths at PEEP max) in the FRM planning view 33, independently of each other. The number of breaths at each step of the recruitment staircase may for instance be in the range of 1-10 breaths. The number of breaths on the recruitment plateau may be the same as the number of breaths on each step of the recruitment staircase. Preferably, however, the number of breaths on the plateau exceeds the number of breaths on each step of the staircase. For example, the number of breaths on the plateau may be in the range of 3-30 breaths.

The recruitment phase starts by increasing PEEP and PIP to the first step of the recruitment staircase, whereafter the breathing apparatus 2 steps through the recruitment staircase up to the maximum PIP and PEEP levels in accordance with the settings in the FRM planning view 33. The incremental limb of the staircase constitutes a pre-conditioning phase mainly serving to gradually prepare the lungs of the patient 2 for ventilation on the maximum PIP level, while the plateau of the staircase constitutes a lung-opening phase mainly serving the purpose of opening collapsed alveoli through high pressure ventilation. Typically, some collapsed alveoli will open-up also during the pre-conditioning phase of the recruitment, whereby the stepwise increase in PEEP serves to keep these newly recruited alveoli open.

The breathing apparatus 2 may, in some embodiments, further be configured to determine an alveolar opening pressure during the recruitment phase. The alveolar opening pressure corresponds to a pressure level at which most previously closed alveoli are re-opened. The alveolar opening pressure may be lower than the set maximum PIP level. There are different means and techniques for determining alveolar opening pressure during lung recruitment manoeuvres, and the breathing apparatus 3 may be devised and configured to use any means and technique known in the art for determining the alveolar opening pressure of the patient 2 during the recruitment phase. For example, the breathing apparatus 2 may comprise or be connected to a carbon dioxide (CO2) module for measuring CO2 in expiration gases exhaled by the patient 3, and to use the measured CO2 values to identify the alveolar opening pressure. The breathing apparatus 2 may, for instance, be configured to compare CO2 measurements (e.g. measurements of end-tidal CO2, VTCO2) obtained at different PIP levels of the incremental limb of the recruitment staircase, and to determine the alveolar opening pressure as the PIP level at which a substantial reduction in expired CO2 is detected.

In some embodiments, the operator of the breathing apparatus 3 may be given the option to bypass the remainder of the recruitment phase upon detection of an alveolar opening pressure that is lower than the set maximum PIP pressure. This functionality may, for example, be implemented by displaying a dialogue window on the display of the breathing apparatus 2 upon detection of the alveolar opening pressure by the breathing apparatus. The dialogue window may comprise information on the detection of the alveolar opening pressure and allow the operator to bypass the remainder of the recruitment phase, e.g. by pressing a button in the dialogue window. Alternatively, the breathing apparatus 2 may be configured to automatically bypass the remainder of the recruitment phase upon detection of the alveolar opening pressure.

Upon bypass of the remainder of the recruitment phase, the breathing apparatus 2 may be configured to go directly to the PEEP titration phase.

FRM: PEEP Titration Phase

During the PEEP titration phase, the breathing apparatus 2 attempts to determine the optimal PEEP. As well known in the art, there are many ways in which a more or less optimal PEEP level of a patient can be identified during a PEEP titration procedure, and the present disclosure is not limited to any particular way of doing so.

Non-limiting examples of parameters that may be used by the breathing apparatus 2 to establish the optimal PEEP is the dynamic compliance of the patient, pressures indicative of the lung pressure of the patient (e.g. measured airway pressure), volumes indicative of the effective lung volume of the patient (e.g. measured tidal volume), gas concentration in expiration gases exhaled by the patient (e.g. expired CO2), blood oxygenation (e.g. peripheral oxygen saturation, SpO2), and a stress index parameter determined from a pressure-volume (P-V) relationship.

In the following, the PEEP titration phase will be described in the context of an exemplary embodiment in which the optimal PEEP of the patient is determined by assessing the dynamic compliance, Cdyn, of the patient's lungs during a stepwise decrease in PEEP. The optimal PEEP may, in this scenario, be determined by finding a closing PEEP corresponding to a PEEP level where alveoli starts to collapse, i.e. a closing PEEP substantially corresponding to the alveolar closing pressure of the patient 2. The optimal PEEP of the patient may then be set by the breathing apparatus 2 to a value that is slightly higher than the determined closing PEEP. Preferably, the optimal PEEP is set in the range of 1-3 cmH2O above closing PEEP, and most preferably to approximately 2 cmH2O above closing PEEP.

Closing PEEP can be determined since Cdyn is expected to change in a predictable way as PEEP is reduced during the PEEP titration phase. A more or less distinct peak in Cdyn is expected just prior to the point in time when alveoli start to cyclically collapse. To avoid high tidal volumes as compliance increases, and to obtain comparable Cdyn values during PEEP titration, the PEEP titration phase is performed in VC ventilation mode. The tidal volume of the VC ventilation is adapted to the relevant patient category and may, for example, be selected by the breathing apparatus 2 based on a predicted bodyweight of the patient 3, e.g. as input to the breathing apparatus 2 by the breathing apparatus operator. As illustrated in upper right corner of FIG. 4, the FRM planning view may comprise an indication of the predicted bodyweight (PBW) of the patient. In the illustrated example, the tidal volume of the VC ventilation may be adjusted by the operator via a setting (VT/PBW) in the FRM planning view 33. The set tidal volume may be expressed in terms of volume of breathing gas per kilo bodyweight, and/or in terms of a total volume of breathing gas per breath. Cdyn may then, for example, be calculated by the breathing apparatus 2 based on a change in airway pressure resulting from delivery of a well-defined tidal volume of breathing gas to the lungs of the patient 3. Consequently, the breathing apparatus 2 may be configured to calculate Cdyn for any given breath during PEEP titration based on set or measured tidal volume and pressure measurements indicative of actual PEEP and PIP obtained by the one or more pressure sensors 25, 25', 25" of the breathing apparatus (see FIG. 1).

The PEEP titration phase starts by first reducing the PEEP level to the PEEP titration start level and then switch from PC to VC ventilation with RR and I:E settings corresponding to ventilation settings used prior to initiation of FRM. The patient 3 is ventilated on each PEEP level for a number of breaths, and a Cdyn value is determined for each breath. The number of breaths on each PEEP level is set by the FRM setting Breaths/step in the FRM planning view 33 and may, for instance, be in the range of 6-15 breaths. When the set number of breaths for a given PEEP step has been delivered to the patient 3, the breathing apparatus 2 reduces PEEP to the next PEEP titration level. In the illustrated example, the size of each PEEP step in the PEEP titration phase is preset to a maximum of 2 cmH2O. If the set PEEP start level is low, the size of each PEEP step may be automatically reduced by the breathing apparatus 2. In other embodiments, the size of each PEEP step in the PEEP titration phase may be set by the operator via a user-adjustable setting in the FRM planning view. The size of each PEEP step in the PEEP titration phase should preferably be in the range of 1-3 cmH20, and most preferably around 2 cmH2O.

The decremental decrease in PEEP during the PEEP titration phase is continued until a maximum Cdyn can be identified, until a set minimum PEEP level is reached, or until a predefined abortion criterion is met, as will be discussed in more detail below. The minimum PEEP level may be preset or set by the operator via an adjustable setting in the FRM planning view 33.

In order to accurately determine Cdyn, the breathing apparatus 3 may be configured to disregard any spontaneous breaths during the PEEP titration phase, meaning that Cdyn may be calculated only for fully controlled breaths during the PEEP titration phase.

If PEEP titration is performed in VC mode, as in the illustrated exemplary embodiment, the PIP of the patient is not directly controlled but a consequence of the combination of set tidal volume and compliance In this case, it is important to adequately handle potentially high PIP during the first PEEP levels of the PEEP titration phase, where the lungs of the patient 3 can be expected to be over distended with a relatively low compliance.

Therefore, as a first lung protective strategy should measured airway pressure exceed the maximum PIP limit (PIP max) during a breath of PEEP titration phase, the breathing apparatus 2 may be configured to cycle off the breath, whereby the volume of breathing gas delivered during the breath will not reach the set tidal volume. As long as a safety valve of the breathing circuit is not opened in this situation (e.g. due to patient coughing or external manipulation), the PEEP titration phase may continue as planned after the prematurely cycled off breath. If the airway pressure of the patient 3 reaches the maximum PIP limit for two breaths at the same PEEP step of the PEEP titration staircase, i.e. if two breaths on the same PEEP step are prematurely cycled off, the breathing apparatus 2 may be configured to immediately (typically within 1-2 breaths) reduce PEEP to the next PEEP level. Cdyn values for prematurely cycled off breaths are not reliable and are not used by the breathing apparatus 2 in the determination of the alveolar closing pressure of the patient 3.

In some situations, in particular during the first steps of PEEP titration in VC mode, PIP may be high enough to have potential detrimental effect on the patient's lungs due to over distension of the lung tissue, yet not high enough to reach the maximum PIP limit. Therefore, as a second lung protective strategy, the breathing apparatus 2 may be configured to monitor PIP during PEEP titration and if the PIP exceeds a secondary PIP limit being lower than the maximum PIP limit for two consecutive breaths, the breathing apparatus may be configured to skip any remaining breaths on the current PEEP step and reduce PEEP to the next PEEP level. The secondary PIP limit thus serves as a maximum PIP limit for consecutive breaths at the respective PEEP step of the PEEP titration phase, For instance, the secondary PIP limit may be 35 cmH2O for a "normal" patient. For obese patients, the secondary PIP limit may be 40-45 cmH2O.

As an alternative lung protective strategy, the breathing apparatus 2 may be configured to immediately reduce PEEP to the next lower PEEP level in response to detection of an airway pressure above the maximum PIP limit if, and only if, no previous PEEP titration step has been successfully completed (i.e. if all previous PEEP steps have been prematurely aborted due to the maximum PIP limit being exceeded). If, on the other hand, one or more previous PEEP steps have been successfully completed, the breathing apparatus 2 may be configured to apply some of the above mentioned lung-protective strategies for consecutive and/or non-consecutive breaths on the same PEEP step.

It should be appreciated that there are other parameters than airway pressure that may be monitored during the PEEP titration phase to avoid potentially harmful levels of ventilation of the patient, and that the above mentioned lung protective strategies may be used for any monitored parameter indicative of a potentially harmful level of ventilation of the patient during PEEP titration in any mode of ventilation.

Consequently, the breathing apparatus 2 may be configured to automatically decrease PEEP to a lower, and typically the next lower PEEP level, in response to a crossing of a threshold value of a monitored parameter indicative of a potentially harmful level of ventilation of the patient 3 during the PEEP titration phase. The breathing apparatus 2 may be configured to decrease PEEP to the next PEEP level the first time the monitored parameter reaches the threshold value. In other embodiments, breathing apparatus 2 may be configured not to reduce the PEEP level when the monitored parameter reaches the threshold value for a first time, but when the monitored parameter reaches the threshold value for at least a second time at the same PEEP level. This has the effect of avoiding too early and uncalled-for abortion of PEEP titration on a certain PEEP level. As described above, there may be a first threshold value for any two breaths at the same PEEP level, and a second and different threshold value for two or more consecutive breaths at the same PEEP level. The effect of using a different threshold value for consecutive and non-consecutive breaths is that premature abortion of PEEP titration on a certain PEEP level can be avoided while still effectively protecting the lungs of the ventilated patient 3. As also described above, the breathing apparatus 2 may be configured to reduce PEEP to a lower PEEP level when the monitored parameter reaches the threshold value for a first time on a current PEEP level only if the threshold value has been reached on at least one previous (higher) PEEP level. If the threshold value has not been reached on any of the previous PEEP levels, the breathing apparatus 2 may be configured not to reduce the PEEP level when the monitored parameter reaches the threshold value for a first time on a current PEEP step, but to reduce PEEP when the monitored parameter reaches the threshold value for at least a second time at the current PEEP level. This has the effect of preventing PEEP from being reduced due to occasional events, such as patient coughing, while ensuring that PEEP is reduced when the patient seems to be ventilated on a potentially harmful level of ventilation.

A third lung protective strategy may also be put in place in order to avoid volutrauma due to stacked breaths in VC mode during PEEP titration. To this end, during the PEEP titration phase, the breathing apparatus 2 may be configured not to deliver a breath normally delivered to the patient 3 in VC mode in response to a detected breathing effort by the patient. The functionality of non-delivery of breaths in response to patient efforts during the PEEP titration phase may be implemented either by actively interrupting the delivery of breaths by the breathing apparatus, or by adjusting a trigger sensitivity of the breathing apparatus 3 during the PEEP titration phase. For example, a trigger level for measured airway pressure may be set to a very low sensitivity level, such as −20 cmH2O, during PEEP titration in order to avoid triggering of breaths.

The breathing apparatus 2 may use different search algorithms for identifying the alveolar closing pressure of the patient 2 during the PEEP titration phase. In an exemplary embodiment, the search algorithm may be adapted to find the alveolar closing pressure of the patient by identifying a closing PEEP at which the Cdyn parameter assumes a maximum value during the PEEP titration phase. This may be achieved by fitting the Cdyn values determined for the respective PEEP steps to a polynomial. The search algorithm should be robust against noise, e.g. due to occasional spontaneous patient activity or external manipulation of the patient. To this end, the algorithm may employ statistical methods for disregarding "non-normal" breaths on each PEEP step, as well as for handling too large deviations in calculated Cdyn values.

For each breath at any given PEEP step, a Cdyn value is calculated and an actual PEEP is measured. The Cdyn values and the measured PEEP values of all breaths at the PEEP step are collected and stored in sorted lists. When Cdyn and PEEP values for the last breath of the PEEP step have been collected, the breathing apparatus 2 is configured to identify a sequence of breaths among the breaths of the PEEP step that has the least standard deviation in Cdyn. The breathing apparatus 2 then calculates representative values of Cdyn and PEEP for the PEEP step as the mean values of Cdyn and PEEP for the identified sequence of breaths. The representative values of Cdyn and PEEP, as well as the Cdyn standard deviation for all PEEP steps are added to a data array that is fitted to a third or higher degree polynomial to determine any local maximum of Cdyn as a function of PEEP. If and when the local maximum has been determined, a check is made as to whether the determined Cdyn maximum lies within the PEEP range covered so far in the PEEP titration phase. If the Cdyn maximum lies within the PEEP titration range covered so far, the PEEP titration phase is aborted and the FRM manoeuvre continues to the re-recruitment phase. By skipping any remaining PEEP steps of the planned PEEP titration phase when a local maximum of Cdyn has been identified, the duration of the FRM manoeuvre and any discomfort to the patient can be minimised. If the determined Cdyn maximum does not lie within the PEEP titration range covered so far, the PEEP titration phase is continued until a local Cdyn maximum lying within the PEEP titration range covered so far has been identified. If no Cdyn maximum can be found, the PEEP titration phase continues until the minimum PEEP level has been reached, or until a predefined abortion criterion is met.

The PEEP value for maximum Cdyn is assumed to correspond to the alveolar closing pressure of the patient and is hence the PEEP value herein referred to as closing PEEP.

In some situations, the breathing apparatus 2 will be unable to determine a reliable maximum Cdyn and hence unable to reliably determine a closing PEEP corresponding to the alveolar closing pressure of the patient. The breathing apparatus may for instance be unable to identify a maximum Cdyn during the PEEP titration phase due to any of, or any combination of, the following reasons:

Noisy Cdyn measurements, e.g. due to too high degree of spontaneous breathing activity by the patient, secretions in an endotracheal tube or the patient circuit of the ventilation system, or external manipulation of the patient;

Constantly falling Cdyn, e.g. due to too low recruitment pressure or too low start level for PEEP titration, or due to the fact that the optimal PEEP is the start level for PEEP titration;

Constantly rising Cdyn, e.g. due to PEEP-independent lungs, i.e. healthy lungs without need for recruitment, or due to high leakage during expiration;

Substantially constant Cdyn, i.e. very small variations in Cdyn during PEEP titration, e.g. due to highly heterogeneous ("non-recruitable") lungs.

The breathing apparatus 2 may be configured to handle all these situations in a similar manner, with only minor differences in the information communicated to the operator.

Whenever a maximum Cdyn cannot be identified during PEEP titration, the breathing apparatus 2 is configured to abort the FRM manoeuvre and to reset ventilation settings, including alarm limits, to the settings used prior to the FRM manoeuvre. The breathing apparatus 2 may further be configured to present information on why a maximum Cdyn could not be successfully identified, including at least one possible root cause to the unsuccessful identification.

The breathing apparatus 2 may further be configured to automatically abort the FRM manoeuvre as soon as it can be established that a closing PEEP cannot be reliably determined. This is advantageous in that the patient is relieved from the discomfort and potential risks associated with the FRM manoeuver as soon as it can be established that the manoeuver will not be successful. The breathing apparatus 2 may, for instance, be configured to abort the FRM manoeuver if at least one predefined abortion criterion for the PEEP titration phase is met. The at least one abortion criterion may comprise a criterion for Cdyn. Preferably, the at least one abortion criterion comprises a criterion for a Cdyn trend established during the PEEP titration phase. For example, the breathing apparatus 2 may be configured to abort the FRM manoeuvre in case a Cdyn trend indicates that no reliable Cdyn maximum is likely to be identified by the breathing apparatus. For instance, if the Cdyn trend indicates a constantly raising Cdyn, a constantly falling Cdyn, or a substantially constant Cdyn, the breathing apparatus may abort the FRM manoeuvre.

If the at least one abortion criterion is met, the breathing apparatus 2 is configured to abort the FRM manoeuvre and return to the ventilation mode and ventilation settings used prior to initiation of the FRM manoeuvre.

Consequently, Cdyn may be monitored and used by the breathing apparatus 2 not only to determine the optimal PEEP but also to establish a trend that can be used to predict whether or not the optimal PEEP can be reliably determined later on during the PEEP titration phase. The ability of the breathing apparatus to predict whether it will be possible to reliably determine an optimal PEEP of the patient later on during the PEEP titration phase, and to abort the FRM manoeuvre if not, is advantageous in that an unsuccessful FRM manoeuvre can be aborted at a very early stage.

Examples of other parameters that may be monitored and used to establish a parameter trend that is indicative on whether or not it will be possible to reliably determine closing PEEP later on during the titration phase is a phase II slope parameter derived from a volumetric capnogram (Vcap), and a stress index derived from a pressure-volume (P-V) relationship. Consequently, the breathing apparatus 2 may use the Vcap phase II slope and/or the stress index to predict whether or not the optimal PEEP can be reliably determined later on during the PEEP titration phase As well known in the art, measurements of expired CO2 and volume can be used to establish a volumetric capnogram, where expired CO2 is plotted against exhaled volume. This allows for breath-to-breath quantification of alveoli that are ventilated but not perfused and measurement of alveolar dead space. The volumetric capnogram of each breath comprises three phases, where the second phase (phase II) represents gas coming from regions that are in the transition between anatomic and alveolar gas compartments. This includes gas emptying from small airways and alveoli that are close to the main airways. During this phase there is an almost linear increase in CO2. A reduction in PEEP will cause the slope of this substantially linear increase in CO2 (phase II slope) to increase until a point in time where alveoli start to collapse, whereafter a further reduction in PEEP will cause the slope to decrease. Consequently, during the PEEP titration phase, the Vcap phase II slope will assume a maximum value at or close to the alveolar closing pressure of the patient. Therefore, the breathing apparatus 2 may be configured to monitor the phase II slope of a volumetric capnogram of the patient during PEEP titration, and to determine an optimal PEEP of the patient based on the PEEP level for which the maximum phase II slope is obtained. The PEEP value for the maximum phase II slope correspond to the closing PEEP.

Furthermore, the breathing apparatus 2 may be configured to establish a trend curve for the phase II slope of the volumetric capnogram covering multiple PEEP steps. Such a trend curve may resemble the phase II trend curve illustrated in FIG. 8 in EP1579882A1. This trend curve may be analysed by the breathing apparatus 2 in the same way the Cdyn trend curve is analysed in the example described above. If, for instance, the phase II slope curve is substantially constant, constantly raising or constantly falling, it can be assumed that it will not be possible to reliably determine a maximum for the phase II slope and thus not possible to reliably determine an optimal PEEP of the patient during the PEEP titration phase. In this case, the breathing apparatus 2 may abort the FRM manoeuvre. The breathing apparatus 2 may be configured to determine the phase II slope on a breath-by-breath basis during PEEP titration, and to process the phase II slope measurements the way the Cdyn measurements are processed in the example described above, e.g. in terms of averaging for each PEEP step, etc.

Stress index is a parameter that is indicative of the pulmonary stress of a ventilated patient, which parameter may be determined by establishing a P-V relationship for a single breath and determining the profile (I.e. the concavity or convexity) of the P-V relationship. The profile is straight (stress index=1) when no stress is present, convex (stress index<1) when there is a risk for overdistension, and concave (stress index>1) when alveoli are opened up during the breath. More Information about the stress index parameter and how to use the stress index in the assessment of pulmonary stress can be found in e.g. U.S. Pat. No. 6,718, 975B2. Typically, at the start of PEEP titration, the lungs of the patient will be partly overdistended, resulting in a stress index>1. However, as PEEP approaches an optimum PEEP for the patient, the stress index will approach one. Consequently, the breathing apparatus 2 may be configured to monitor the stress index of the patient during the PEEP titration phase, and to determine an optimal PEEP of the patient based on the PEEP value for which the monitored stress index assumes a value of one.

Furthermore, the breathing apparatus 2 may be configured to establish a trend curve for the stress index covering multiple PEEP steps. Such a trend curve should approach one if the optimal PEEP of the patient is likely to be found during the PEEP titration phase. If the stress index trend curve does not approach one (e.g. if the stress index trend curve is substantially constant or even diverging from stress index=1), the breathing apparatus 2 can predict that it will not be possible to reliably determine an optimal PEEP of the patient during the PEEP titration phase, whereby the breathing apparatus 2 may abort the FRM manoeuvre. The breathing apparatus 2 may be configured to determine the stress index on a breath-by-breath basis during PEEP titration, and to process the stress index measurements the way the Cdyn measurements are processed in the example described above, e.g. in terms of averaging for each PEEP step, etc.

Above, it has been described that the breathing apparatus may be configured to predict if it will be possible to reliably determine an optimal PEEP later on during the PEEP titration phase based on a trend of a monitored parameter (e.g. Cdyn, Vcap phase II slope or stress index), and to abort the FRM manoeuvre if reliable determination of optimal PEEP will not be possible. It should be noted that the breathing apparatus may also be configured to abort the FRM manoeuvre if the quality of at least one measurement signal required for determination of the monitored parameter is poor. The breathing apparatus 2 may be configured to assess the signal quality and to predict whether or not it will be possible to reliably determine the optimal PEEP of the patient given the quality of the at least one measurement signal. If, based on the quality of the at least one measurement signal, it is predicted that an optimal PEEP cannot be reliably determined, the breathing apparatus 2 may abort the FRM manoeuvre.

Figure 5:
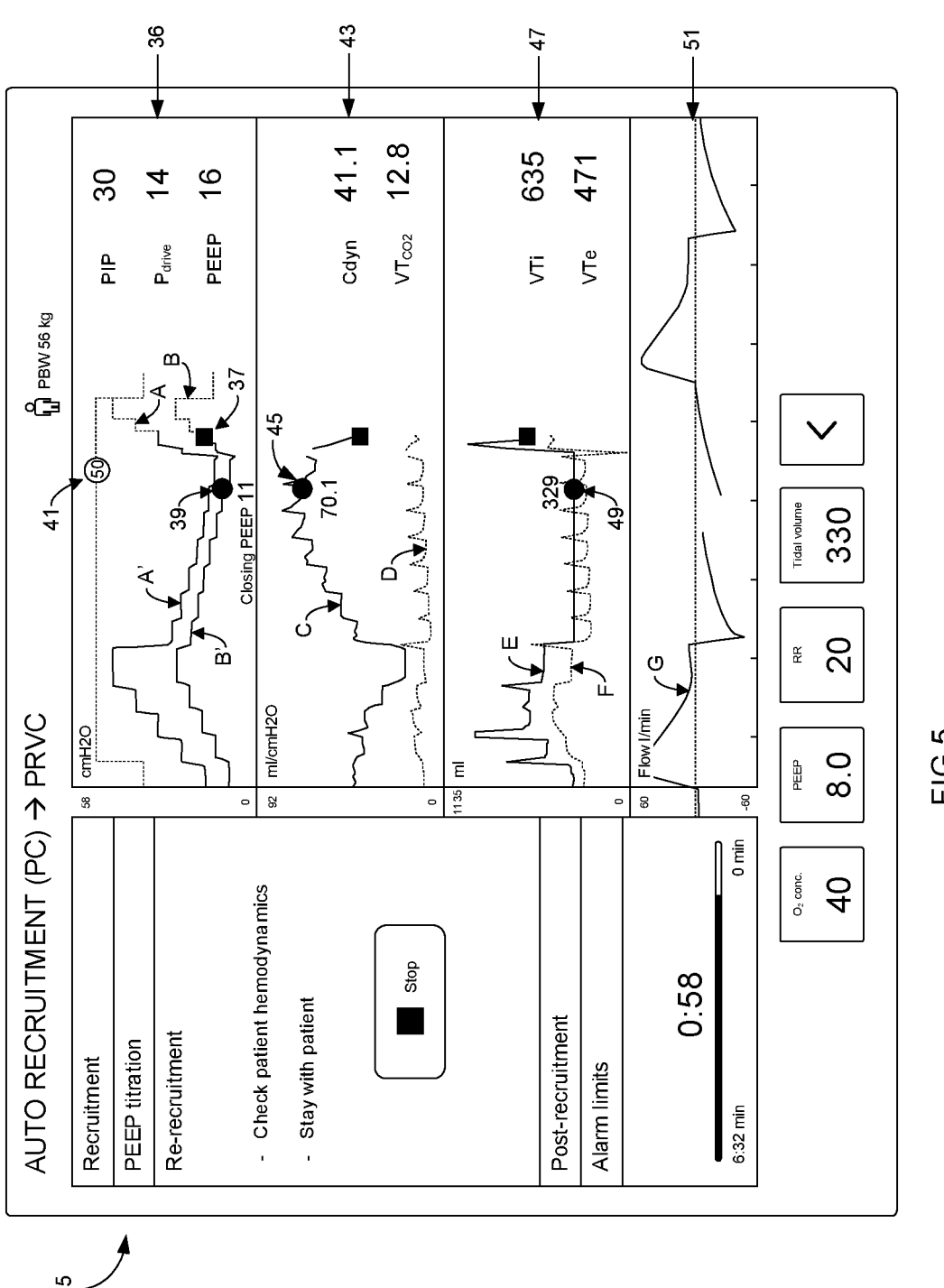
FIG. 5 illustrates an exemplary GUI view for monitoring an automated FRM manoeuvre.

FIG. 5 illustrates an exemplary FRM workflow view 35 of the OLT interface. When the operator is done planning the FRM manoeuvre in the FRM planning view 33 of FIG. 4 and chooses to confirm the FRM settings, e.g. by pressing a continue button displayed in the FRM planning view, the breathing apparatus 3 displays the FRM workflow view 35 of FIG. 5, through which the operator may initiate and monitor the FRM manoeuvre.

The exemplary FRM workflow view 35 in FIG. 5 comprises a pressure display field 36 illustrating the planned pressure trajectories A and B for PIP and PEEP. As the FRM manoeuvre progresses, the planned PIP and PEEP trajectories A and B are replaced by curves A' and B' representing measured PIP and PEEP. The pressure display field 36 comprises a position indicator 37 indicating in real time a current position along any or both of the pressure trajectories for PIP and PEEP. The pressure display field 36 further comprises a closing PEEP indicator 39 indicating the value and positon of the closing PEEP determined during PEEP titration. The pressure display field 36 further comprise a PIP limit indicator 41 indicating the maximum PIP limit set in the FRM planning view 33. Yet further, the pressure display field 36 comprises current values of PIP, Pdrive and PEEP.

The exemplary FRM workflow view 35 further comprises a Cdyn display field 43. The Cdyn display field comprises a Cdyn curve C representing Cdyn values determined for the breaths of the FRM manoeuvre. The Cdyn display field 43 further comprises a maximum Cdyn indicator 45 indicating the value and position of the maximum Cdyn determined during PEEP titration. In the illustrated embodiment, the breathing apparatus 3 is devise with a $CO_2$ module for measuring $CO_2$ in expiration gases exhaled by the patient 3, and the Cdyn display field 43 further comprises a $CO_2$ elimination curve D representing the tidal volume of $CO_2$ elimination (VTCO2) during the breaths of the FRM manoeuvre. The Cdyn display field 43 further comprises current values of Cdyn and VTCO2. In cases where other parameters than Cdyn are used to determine the optimal PEEP of the patient, such as the above mentioned phase II slope parameter or stress index parameter, trend curves and/or current values for these parameters may be displayed instead of, or in addition to, the Cdyn curve C and the current value of Cdyn.

The FRM workflow view 35 further comprises a volume display field 47. The volume display field 35 comprises an inspiratory volume curve E representing the inspiratory tidal volume, VTi, during breaths of the FRM manoeuvre. The tidal volume display field 47 further comprises a tidal volume indicator 49 indicating the inspiratory tidal volume of the patient 3 at closing PEEP. Information on tidal volume at closing PEEP is somewhat redundant in the illustrated embodiment where PEEP titration is performed in VC mode using constant tidal volume, but is highly relevant in other conceivable embodiments in which PEEP titration is performed in PC mode. The volume display field 47 further comprises an expiratory volume curve F representing the expiratory tidal volume, VTe, of breaths of the FRM manoeuvre. The volume display field 47 further comprises current values of VTi and VTe.

The above mentioned curves A', B', C-F of the FRM workflow view 35 thus constitute real time plots of breath-to-breath trend curves for the parameters PIP, PEEP, Cdyn, VTCO2, VTi and VTe.

The FRM workflow view 35 further comprises a flow display field 51. The flow display field comprises a flow curve G representing respiratory flow during the most recent breath or breaths. The exemplary flow curve G is a real time plot of airway flow. In some embodiments (not shown), the FRM workflow view 35 may comprise at least one interactive element, such as one or more buttons, allowing the operator to toggle between real time plots of measured flow, pressure, trans-pulmonary pressure, and/or Edi signals, possibly in combination with numeric presentation of additional parameters.

In the illustrated exemplary embodiment, Cdyn max (70,1) was found for a closing PEEP of 11 cmH2O during the PEEP titration phase.

FRM: Re-recruitment

The re-recruitment phase of the FRM manoeuvre is a shorter version of the recruitment phase. The purpose of the re-recruitment phase is to re-open any alveoli that have collapsed during the PEEP-titration phase, and in particular during ventilation at the lowest steps of the PEEP titration staircase.

In the illustrated embodiment, when going from the PEEP titration phase to the re-recruitment phase, the breathing apparatus 2 changes ventilation mode from the VC mode of the PEEP titration phase to PC mode. Like in the recruitment phase, the PEEP and PIP are incrementally increased up to maximum PEEP and PIP values to gradually prepare the lungs of the patient for high pressure ventilation. The maximum PIP is maintained for a number of breaths to ensure that any alveoli that have collapsed during the PEEP titration phase are re-opened during the re-recruitment phase.

To serve the purpose of re-opening any closed alveoli, the maximum PIP at the plateau of the re-recruitment staircase should be higher than the alveolar opening pressure of the patient 3. If the breathing apparatus 2 is devised and configured to determine the alveolar opening pressure of the patient 3 during the recruitment phase, e.g. from expiratory CO2 measurements as explained above, the maximum PIP of the re-recruitment phase may be automatically set to a value that is slightly higher than the alveolar opening pressure. This means that the maximum PIP of the re-recruitment phase may be set to a lower value than the maximum PIP of the recruitment phase, thereby reducing the adverse effects of high pressure ventilation. In another exemplary embodiment, the re-recruitment phase may be carried out with the same settings as the recruitment phase but with a reduced number of breaths per PEEP step (e.g. half the number), and with a reduced number of breaths at the maximum PEEP (and maximum PIP) plateau (e.g. half the number). In the illustrated embodiment, this means that the recruitment parameters PEEP max, PIP max, PEEP incr/step and Recruitment rate in the FRM planning view shown in FIG. 4 can be used also for the re-recruitment phase, whereas the number of breaths per PEEP step and the number of breaths at maximum PEEP may be set to e.g. half the values of the respective recruitment parameters Breaths/step and Breaths at PEEP max, round-up to the nearest integer.

FRM: Post-RM

After the re-recruitment phase of the FRM manoeuvre, the breathing apparatus 2 enters the post-RM phase and starts ventilating the patient with optimised ventilation settings determined during the FRM manoeuvre. The optimised ventilation settings comprises at least the optimal PEEP determined during PEEP titration.

Furthermore, if post-RM ventilation is carried out in PC mode, the breathing apparatus enters the post-RM phase with a post-RM driving pressure that is optimised to the changed lung dynamics of the patient 3. This optimised post-RM driving pressure is hereinafter referred to as the optimal driving pressure (optimal Pdrive). The optimal driving pressure may be automatically determined by the breathing apparatus 2 based on measured PEEP and Cdyn values during the PEEP titration phase. In one exemplary embodiment, the breathing apparatus 2 is configured to determine an optimal driving pressure for post-RM ventilation which, given the optimal PEEP and a PEEP-Cdyn relationship established during the PEEP titration phase, results in a tidal volume corresponding to the tidal volume set for the PEEP titration phase. The optimal driving pressure may, for instance, be set to $VT_{desired}/C_{dyn\_opt}$, where $VT_{desired}$ is a desired tidal volume for the post-RM phase, e.g. corresponding to the tidal volume set for the PEEP titration phase (via the VT/PBW setting in the planning view 33), and $C_{dyn\_opt}$ is the Cdyn value corresponding to the optimal PEEP.

If post-RM ventilation is carried out in VC mode, the breathing apparatus enters the post-RM phase with a tidal volume corresponding to the tidal volume set for the PEEP titration phase. Alternatively, the tidal volume of post-RM VC ventilation may be automatically set to correspond to a tidal volume set for a period of baseline ventilation preceding the FRM manoeuvre, i.e. to a tidal volume set for pre-RM VC ventilation.

When entering into the post-RM phase, the breathing apparatus automatically switches ventilation mode to a predefined ventilation mode that is either automatically determined by the breathing apparatus 2 or preset by the breathing apparatus operator, e.g. in the FRM planning view of the OLT tool. All post-RM ventilation settings except for PEEP and driving pressure (in PC mode) or tidal volume (in VC mode) may be initiated from corresponding settings of the baseline ventilation preceding the FRM manoeuvre.

Preferably, the breathing apparatus 2 is configured to automatically switch to a previous ventilation mode used during baseline ventilation preceding the FRM manoeuvre, and to enter the post-RM phase in the previous ventilation mode but with optimised ventilation settings, as described above. That the breathing apparatus 2 is configured to automatically return to the ventilation mode that was used prior to the FRM manoeuvre is advantageous in that manual workload is minimised and in that the breathing apparatus operator does not have to remember the ventilation mode or ventilation settings used prior to the FRM manoeuvre.

The post-RM phase is an evaluation phase in which the patient 3 is ventilated at the optimal PEEP for a few breaths (typically around five breaths) during which post-RM comparison data to be compared with the pre-RM comparison data obtained during the pre-RM phase is collected. As mentioned above, the comparison data may e.g. comprise data on Pdrive, Cdyn, PEEP, PIP and VTi.

Following the post-RM collection of comparison data, the breathing apparatus 2 is configured to present, to the breathing apparatus operator, evaluation data indicative of the effect of the FRM manoeuvre on the patient 3. The evaluation data comprises or is derived from the comparison data collected during the pre-RM phase (pre-RM comparison data) and the comparison data collected during the post-RM phase (post-RM comparison data). The evaluation data may comprise numerical values and/or a graphical representation of the pre- and post-RM comparison data. Preferably, the evaluation data comprises numerical values and/or graphical representations of at least pre- and post-RM Pdrive and Cdyn values. For instance, the evaluation data may comprise a comparison table including numerical values for one or more of Pdrive, Cdyn, and VTi for both the pre-RM phase and the post-RM phase. Instead of, or in addition to, numerical values of pre-RM and post-RM comparison data, the evaluation data may comprise symbols indicating whether the parameters of the comparison data, e.g., Pdrive, Cdyn, and VTti, have improved or not improved as a result of the FRM manoeuvre. For example, the parameters may be displayed in association with graphics, such as a respective symbol or graph, indicating whether the respective parameters have improved or not improved as a result of the FRM. It should be appreciated that the pre- and post-RM compari- son data, and thus the evaluation data presented to the operator, may comprise other key respiratory parameters than those mentioned above.

Figure 6:
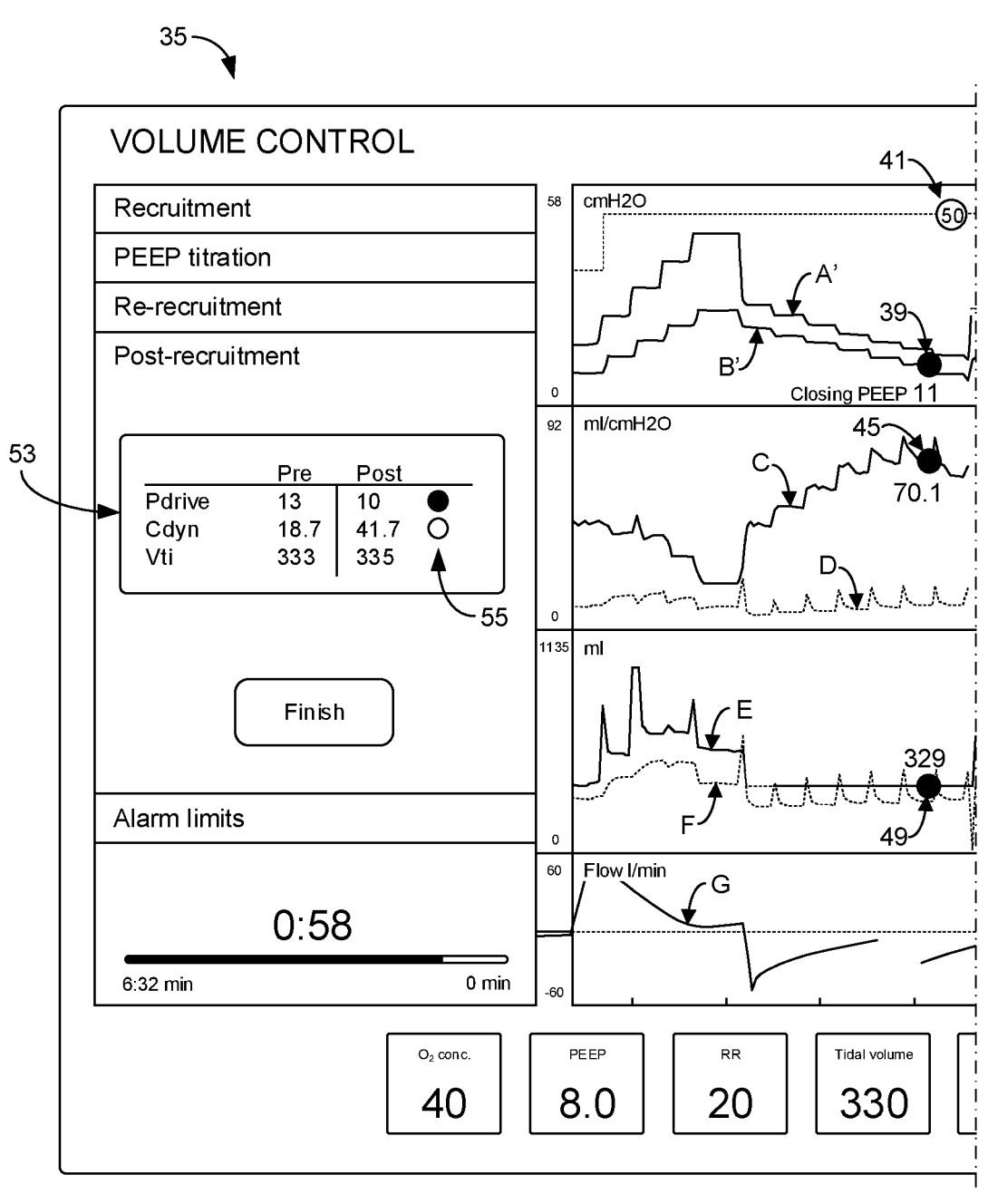
FIG. 6 illustrates an exemplary GUI view for evaluating an automated FRM manoeuvre.

FIG. 6 illustrates an exemplary embodiment in which the evaluation data is displayed in a comparison table 53 of the RM workflow view 35 of the OLT interface. In this exemplary embodiment, the evaluation data comprise numerical values for pre- and post-RM Pdrive, Cdyn and VTi, as well as symbols 55 indicating whether or not there has been any improvement in Cdyn or Pdrive as a result of FRM. Each symbol may be provided with a colour indicating either an improvement (e.g. green colour), no substantial change (e.g. white colour), or a deterioration (e.g. orange colour) in the associated parameter.

After the post-RM collection of comparison data, the breathing apparatus 2 is further configured to present, to the breathing apparatus operator, suggestions on optimised ventilation settings for the new baseline ventilation following the FRM manoeuvre, which ventilation settings are based on one or more parameters determined during the PEEP titra- tion phase. The suggested ventilation settings comprises at least a suggested PEEP for new baseline ventilation, which suggested PEEP may correspond to the optimal PEEP set for the post-RM phase. The suggested ventilation settings may further comprise a suggested driving pressure for new baseline ventilation in PC mode, which suggested driving pressure corresponds to the optimal driving pressure used during the post-RM phase (if performed in PC mode). The suggested ventilation settings may further comprise a sug- gested tidal volume for new baseline ventilation in VC mode, which suggested tidal volume corresponds to the tidal volume used during the post-RM phase (if performed in VC mode).

The suggested ventilation settings may be displayed in association with the evaluation data, thereby indicating to the operator the ventilation settings for which the post-RM comparison data were obtained. For example, the breathing apparatus 2 may be configured to display the suggested ventilation settings in association with the comparison table 53. The breathing apparatus 2 may further be configured to prompt the operator to accept the suggested ventilation settings for new baseline ventilation, e.g. by causing an accept button to be displayed in relation to the suggested ventilation settings. In this way, the operator can easily compare the pre-RM comparison data with the post-RM comparison data and chose to accept the suggested ventila- tion settings only if ventilation with the suggested ventila- tion settings (i.e. post-RM ventilation) has shown a positive effect on the ventilated patient. That ventilation with the suggested ventilation settings shows a positive effect on the ventilated patient indicates that the suggested ventilation settings are better tailored to the changed lung dynamics of the patient than the pre-RM ventilation settings. Further- more, assuming that the pre-RM ventilation settings were properly adjusted, it indicates that the FRM manoeuvre was successful and that alveoli have been successfully recruited.

If the operator chooses to accept the suggested ventilation settings, the breathing apparatus 2 continues to ventilate the patient 3 using the suggested ventilation settings used during the post-PM phase. No changes in ventilation mode or ventilation settings are made. Consequently, by simply accepting the optimised ventilation settings suggested by the breathing apparatus 2, the patient will automatically be ventilated using the same ventilation mode after the FRM manoeuvre as before the FRM manoeuvre, with optimised ventilation settings adapted to changes in lung dynamics caused by the FRM manoeuvre.

If, on the other hand, the operator chooses not to accept the suggested ventilation settings, or does not actively choose to accept the suggested ventilation settings for a predetermined acceptance time of e.g. 1-5 minutes, the breathing apparatus may be configured to revert to all or some of the pre-RM ventilation settings, including pre-RM ventilation settings for PEEP and driving pressure (in PC mode) and tidal volume (in VC mode). Consequently, the breathing apparatus 2 may be configured to automatically revert to settings that may be regarded as "safe settings" should the breathing apparatus operator not accept the suggested ventilation settings within a predetermined accep- tance time. This feature has the effect of improving patient safety as there is always a risk that ventilation settings that are initiated without involvement of a clinician are not suited for long-term ventilation of the patient. There may, for instance, be situations where ventilation settings should be optimised with regard to other parameters than the dynamic compliance of the patient.

Of course, the breathing apparatus 2 may also be config- ured to present the suggested ventilation settings with pos- sibilities for the operator to modify the settings before accepting them, i.e. in form of user-adjustable ventilation settings. Thus, the finally selected ventilation settings for new baseline ventilation following the FRM manoeuvre may deviate from the suggested ventilation settings.

When the operator has accepted or denied the suggested ventilation settings, or when the predetermined acceptance time has lapsed, the FRM manoeuvre is ended and the breathing apparatus 2 displays the view that was displayed on the display 32 of the breathing apparatus prior to entering the FRM planning view 33 of the OLT tool.

Before ending the FRM manoeuvre, however, the breath- ing apparatus 2 is configured to save and store an FRM recording comprising characteristics of the FRM manoeuvre in the memory 31 of the computer 15. The characteristics of the FRM recording comprises the FRM settings set in the FRM planning view 33, the evaluation data comprising the pre-RM and post-RM comparison data, and the suggested and finally selected ventilation settings for new baseline ventilation following the FRM manoeuvre. The FRM recording also comprises the breath-by-breath trend data from which the curves A', B', C-F in the workflow view 35 were generated in real time during the FRM manoeuvre, i.e. breath-by-breath trend data for the parameters PIP, Pdrive, PEEP, Cdyn, VTCO2, VTi and VTe.

The characteristics of the recordings of historical FRM manoeuvres can be studied by the operator via an FRM trend view (not shown) of the OLT tool, or exported to another software application for subsequent analysis. The breath- by-breath trend data of the recordings enables the breathing apparatus 2 to present any of, or any combination of, the breath-by-breath trend curves A', B', C-F from previous FRM manoeuvres to the operator, in order for the operator to study the curve(s) retrospectively. Such a breath-by- breath trend curve from a previous FRM manoeuvre is hereinafter referred to as a trend curve recording. The breathing apparatus 2 may be configured to display trend curve recordings for one or more of the parameters PIP, Pdrive, PEEP, Cdyn, VTCO2, VTi and VTe in the FRM trend view. The breathing apparatus 2 may further be configured to display, in association with the one or more trend curve recordings, any of, or any combination of, the FRM settings of the recorded FRM manoeuvre, the evaluation data of the recorded FRM manoeuvre, and the suggested and finally selected ventilation settings for new baseline ventilation following the recorded FRM manoeuvre. If no maximum Cdyn was found during PEEP titration, information (e.g. the root cause) on why Cdyn was not found may also be displayed.

Before ending the FRM manoeuvre, the breathing apparatus 2 may further be configured to automatically adjust relevant alarm limits. Some alarm limits may be reset to the limits used prior to the FRM manoeuvre while other alarm limits may, if the breathing apparatus operator has accepted the suggested ventilation settings, be set based on the suggested ventilation settings for new baseline ventilation following the FRM manoeuvre. Consequently, the breathing apparatus 2 may be configured to automatically adjust alarm limits for relevant respiratory parameters based on the suggested ventilation settings. For example, the breathing apparatus 2 may be configured to automatically adjust the alarm limits for maximum PIP, maximum PEEP, and/or a minimum PEEP, based on the suggested ventilation settings. The alarm limit for maximum and/or minimum PEEP may be adjusted based on the optimal PEEP suggested for new baseline ventilation following the FRM manoeuvre. The alarm limit for maximum PIP may be adjusted based on the optimal PEEP and the optimal driving pressure suggested for the new baseline ventilation following the FRM manoeuvre. This driving pressure may be any of a driving pressure used prior to the FRM manoeuvre (if no changes in Pdrive are suggested) or a new driving pressure suggested for the new baseline ventilation following the FRM manoeuvre. The feature of automatically updating the alarm limits is advantageous in that in minimises manual workload and improves patient safety since the breathing apparatus operator does not have remember to update the alarm limits to suit the changed lung dynamics of the patient 3 following the FRM manoeuvre.

The breathing apparatus 2 may further be configured to display the new alarm limits to the operator, and, optionally, to prompt the operator to accept the new alarm limits before they are put into use. Of course, the new alarm limit settings may be user-adjustable in order for the operator to adjust the settings before accepting them for use.

The Quick Recruitment Manoeuvre-QRM

The exemplary QRM manoeuvre illustrated in FIG. 3 will now be described in more detail with reference to FIGS. 7 and 8. The QRM manoeuvre and the procedure for carrying out an QRM manoeuvre may include the following phases:

1) A planning phase for planning the QRM manoeuvre by selecting recruitment and post-RM settings;

2) A pre-RM phase involving collection of comparison data indicative of the situation prior to QRM;

3) A recruitment phase for opening up collapsed alveoli, comprising:

a. a recruitment pre-conditioning phase of stepwise increase of PEEP and PIP to prepare lung for recruitment, and b. a plateau recruitment phase involving a potentially prolonged last step of the recruitment staircase, and 4) A post-RM phase involving ventilation with pre-defined PEEP, with initial collection of comparison data for comparison with pre-RM comparison data.

QRM: Planning Phase

In general, the planning phase of the QRM manoeuvre is similar to the planning phase of the FRM manoeuvre except for minor differences in the range of adjustable settings in the planning view of the respective manoeuvre. An exemplary QRM planning view 57 comprising QRM settings for configuring the QRM manoeuvre is illustrated in FIG. 7.

Figure 7:
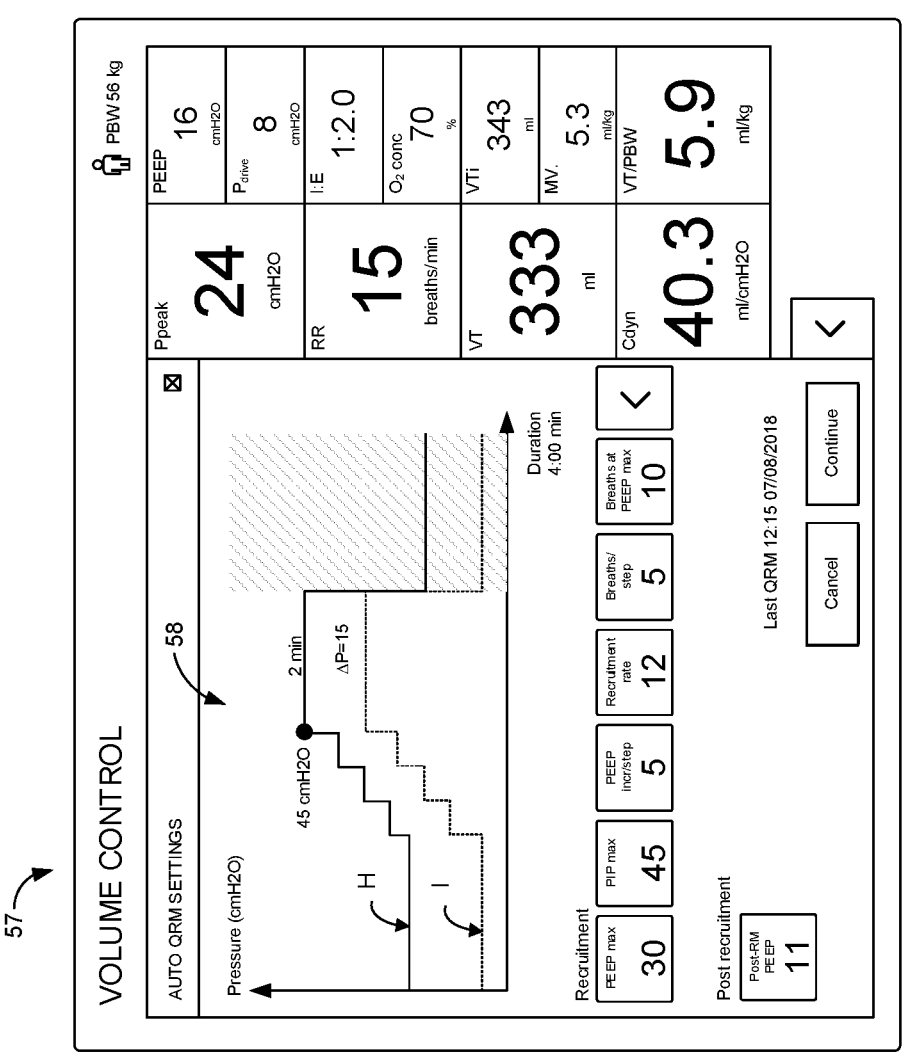
FIG. 7 illustrates an exemplary GUI view for planning an automated QRM manoeuvre.

As shown in FIG. 7, the QRM planning view 57 for planning the QRM manoeuvre is very similar to the FRM planning view 33 for planning the FRM manoeuvre, illustrated in FIG. 4. Just like the FRM planning view 33, the QRM planning view 57 includes settings for maximum PEEP (PEEP max), maximum PIP (PIP max), incremental increase in PEEP (PEEP incr/step), respiratory rate (Recruitment rate), breaths per PEEP step during recruitment (Breaths/step), and breaths at maximum PEEP (Breaths at PEEP max). The QRM planning view is further seen to comprise a setting for post-RM PEEP (Post-RM PEEP), which setting will be described in more detail below.

Similar to the FRM planning view 33, the QRM planning view 57 further comprises a visualisation 58 of the planned pressure trajectories for the QRM manoeuvre. In the pressure trajectory visualisation, reference sign H denotes a planned PIP trajectory and reference sign I denotes a planned PEEP trajectory for the QRM manoeuvre.

When not preceded by a previous FRM manoeuvre, the QRM settings are default settings initiated for the relevant patient category. If, on the other hand, an FRM manoeuvre has previously been performed for the same patient 3, the settings used for the previous FRM may be used as proposed settings for the QRM manoeuvre, or for multiple QRM manoeuvres following an FRM manoeuvre. Preferably, also results from the previously performed FRM manoeuvre, e.g. the optimal PEEP determined during the PEEP titration phase of previous FRM manoeuvre, are used to initiate the settings for the QRM manoeuvre.

By using the settings and/or results from a previous FRM manoeuvre to initiate suggested settings for the QRM manoeuvre, the QRM can be initiated quickly, with a minimum of manual input of information to the breathing apparatus.

In the illustrated embodiment, the QRM is assumed to be performed for the same patient 3 as the FRM manoeuvre described with reference to FIGS. 4-6, at a later point in time. Some QRM settings in the QRM planning view 57 may be initiated from the settings of the previous FRM manoeuvre. This applies, for example, to the QRM settings PEEP incr/step, Recruitment rate, Breaths/step and Breaths at PEEP max. It may, in some embodiments, also apply to the QRM settings PIP max and/or PEEP max defining the maximum PIP and maximum PEEP of the recruitment phase of the QRM manoeuvre. Other QRM settings are initiated from the result of the FRM manoeuvre. This applies, for example, to the QRM setting for Post-RM PEEP. It may, in some embodiments, also apply to the QRM settings PIP max and/or PEEP max.

In embodiments where the PIP max and/or PEEP max settings of the QRM manoeuvre are initiated from results of the FRM manoeuvre, the settings may be initiated based on e.g. the optimal PEEP and/or the optimal driving pressure determined during the PEEP titration phase of the FRM manoeuvre. In embodiments where the optimal PEEP is determined based on a maximum Cdyn of the PEEP titration phase, this means that the PIP max and/or PEEP max settings of the QRM manoeuvre are initiated from Cdyn values obtained for different pressure levels during the PEEP titration phase of the previous FRM manoeuvre. Instead, or in addition, the PIP max and/or PEEP max settings may be initiated based on an alveolar opening pressure of the patient 3, as determined during the recruitment phase of the previous FRM manoeuvre. An effect of using results from a previous FRM manoeuvre in the initiation of the PIP max and PEEP max settings for the QRM manoeuvre is that the maximum pressure levels can be set in relation to known lung dynamics of the patient. In this way, the maximum PIP level may be set to a lower level than if it was to be set to guarantee proper recruitment of alveoli without knowledge on the lung dynamics of the patient.

The setting for post-RM PEEP of the QRM manoeuvre is preferably initiated based on the optimal PEEP determined during the PEEP titration phase of the previous FRM manoeuvre. Preferably, the post-RM PEEP setting of the QRM manoeuvre is set to substantially correspond to the optimal PEEP determined during the FRM manoeuvre. Since the pressure trajectories for PEEP and PIP during QRM are set to resemble the pressure trajectories during the recruitment phase of the previous FRM manoeuvre, it can be assumed that the lung dynamics of the patient will be affected in a similar way by the QRM manoeuvre as by the FRM manoeuvre, and thus that a post-QRM PEEP corresponding to the optimal PEEP determined during FRM will be well-adapted to the post-QRM lung dynamics of the patient.

When the QRM settings are accepted by the breathing apparatus operator, the QRM planning view 57 is closed and a QRM workflow view similar to the FRM workflow view 35 in FIG. 4 is opened.

Figure 8:
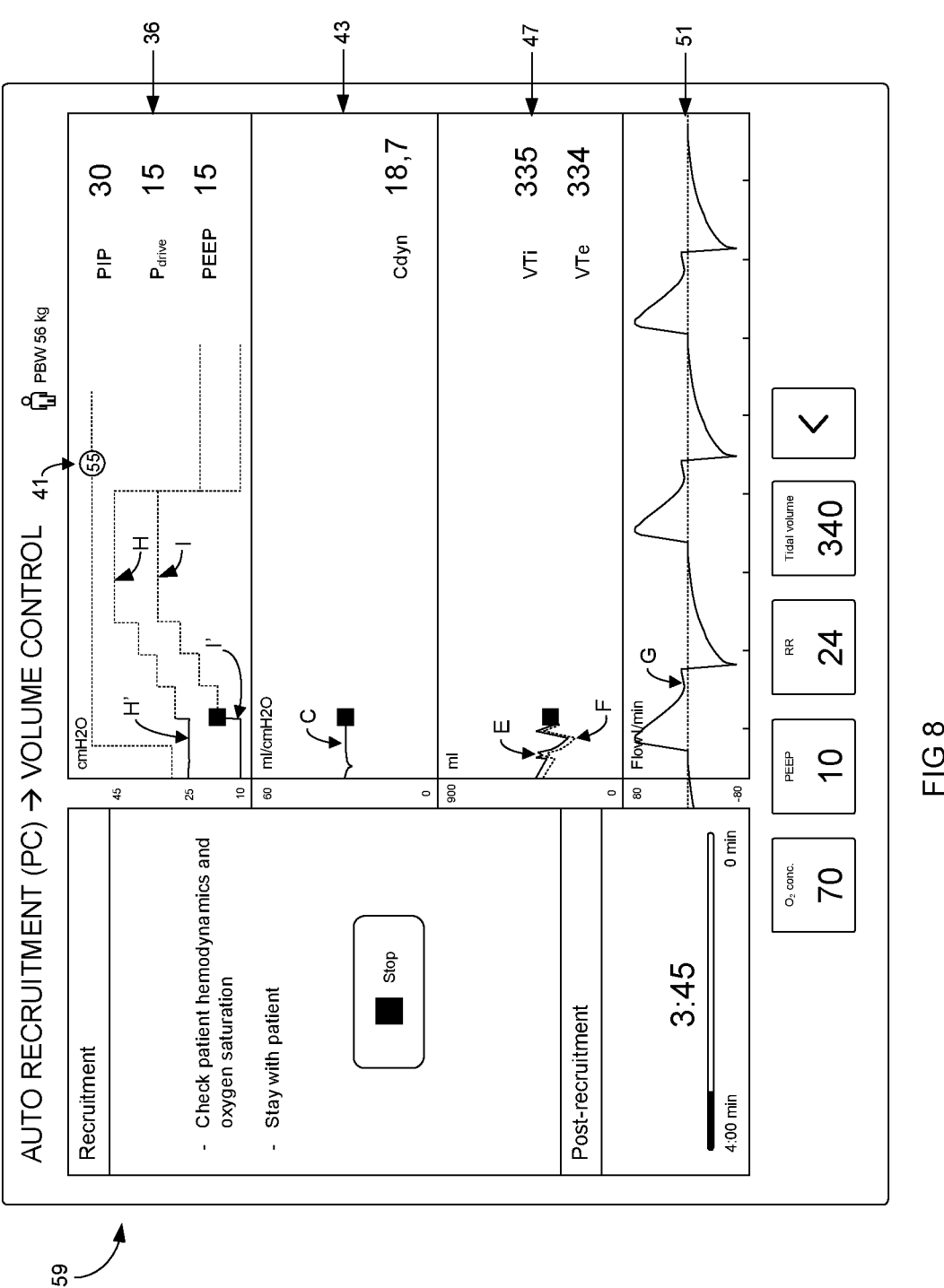
FIG. 8 illustrates an exemplary GUI view for monitoring an automated QRM manoeuvre.

An exemplary QRM workflow view 59 is illustrated in FIG. 8. As mentioned above, the QRM workflow view 59 is similar to the FRM workflow view 35, illustrated in FIG. 4, and same reference numerals in the different views are used to denote the same elements. The main difference between the views is that, in the pressure display field 36 of the QRM workflow view 59, the planned and measured PIP and PEEP trajectories H, I, H', I' for the QRM manoeuvre have replaced the planned and measured PIP and PEEP trajectories A, B, A', B' in the FRM workflow view 35.

Once the QRM manoeuvre is initiated by the operator, e.g. by actuating a button in the QRM workflow view 59, the breathing apparatus 2 initiates the QRM manoeuvre and enters the pre-RM phase of the QRM manoeuvre.

QRM: Pre-RM Phase

The pre-RM phase of the QRM manoeuvre is typically identical to the pre-RM phase of the FRM manoeuvre. In short, this means that the breathing apparatus 2 ventilates the patient 3 for a few breaths with a current ventilation mode and current ventilation settings, and collects pre-RM comparison data to be compared with post-RM comparison collected during the post-RM phase following the recruitment phase of the QRM manoeuvre. The breathing apparatus further changes alarm limits for maximum PEEP and maximum PIP, based on the QRM settings PEEP max and PIP max, and pre-mutes alarms for a predetermined time period (e.g. 2 minutes) to avoid minute ventilation alarms and/or CO2 alarms. If the current ventilation mode is not a PC mode, the breathing apparatus changes 2 ventilation mode to PC mode after the data collection period of the pre-RM phase. This may, for instance, be achieved by setting a driving pressure to reach a previous tidal volume, an inspiration-to-expiration ratio I:E to 1:1, and a respiratory rate in accordance with the Recruitment rate set in the QRM planning view 57. The breathing apparatus 2 then starts ventilating the patient 3 in PC mode at a ventilation level constituting the base level of the QRM recruitment staircase.

In all other aspects, the pre-RM phase of the QRM manoeuvre corresponds to the pre-RM phase of the FRM manoeuvre.

QRM: Recruitment Phase

The recruitment phase of the QRM manoeuvre is similar to the recruitment phase of the FRM manoeuvre. The breathing apparatus 2 steps through the QRM recruitment staircase based on the QRM settings of the QRM planning view 57 in the way the breathing apparatus steps through the FRM recruitment staircase based on the FRM settings of the FRM planning view 33 during the FRM manoeuvre. As mentioned above, the settings for maximum PEEP and/or maximum PIP of the QRM staircase may differ from the maximum PEEP and/or maximum PIP used for the FRM manoeuvre. In all other aspects, the QRM recruitment staircase resembles the FRM recruitment staircase.

QRM: Post-RM Phase

After the recruitment phase of the QRM manoeuvre, the breathing apparatus 2 enters the post-RM phase of the QRM manoeuvre. The post-RM phase of the QRM manoeuvre is similar to the post-RM phase of the FRM manoeuvre, except for the selection of PEEP (post-RM PEEP).

In the FRM manoeuvre, the breathing apparatus 2 may enter the post-RM phase with an optimal PEEP determined from measurements made during the PEEP titration phase. In the QRM manoeuvre, however, where there is no PEEP titration phase, the breathing apparatus 2 enters the post-RM phase with a ventilation mode and ventilation settings corresponding to a ventilation mode and ventilation settings used during baseline ventilation preceding the QRM manoeuvre, except for the setting of PEEP. The post-RM PEEP is set in accordance with the Post-RM PEEP setting in the QRM planning view 57, as described above. Consequently, the breathing apparatus 2 typically enters the post-RM phase of the QRM manoeuvre with a PEEP that is set based on an optimal PEEP determined during a PEEP titration phase of a previously performed FRM manoeuvre for the same patient. As described above, this has the effect of setting a PEEP for the post-RM phase of the QRM manoeuvre (and typically for the new baseline ventilation following the QRM manoeuvre) which, assumingly, is well-adapted to the post-RM lung dynamics of the ventilated patient.

In all other aspects, the post-RM phase of the QRM manoeuvre corresponds to the post-RM phase of the FRM manoeuvre, described above.

In short, this means that the breathing apparatus 2 may ventilate the patient 3 for a few breaths using the set post-RM PEEP while collecting post-RM comparison data; present evaluation data indicative of the effect of the QRM manoeuvre to the breathing apparatus operator; prompt the operator to accept suggested ventilation settings based on the presented evaluation data; save and store a recording of characteristics of the QRM manoeuvre for subsequent post-QRM analysis; set new alarm limits for relevant respiratory parameters, such as maximum PEEP, maximum PIP and/or minimum PEEP, based on the set post-RM PEEP; and, optionally, prompt the operator to accept the new alarm setting before it is put into use.

The QRM manoeuvre may also be performed without the evaluation phase, whereby the manoeuvre does not comprise collection of pre- or post-RM comparison data, nor presentation of evaluation data to the operator. In this case, the operator is not prompted to acknowledge or accept the suggested ventilation settings (comprising at least the Post-RM PEEP setting). Instead, the breathing apparatus is configured to use the Post-RM PEEP setting during the new baseline ventilation following the QRM manoeuvre without acknowledgement from the operator.

It should be appreciated that whereas actions and method steps involving the supply of breathing gas to the patient 3 are typically performed by the breathing apparatus 2 of the ventilation system 1, other actions and method steps of the above described FRM and QRM manoeuvres may be performed by sub-systems or devices forming part of the ventilation system, such as a patient monitoring system (not shown) for monitoring the patient 3 and the effects on the patient of the mechanical ventilation. For example, the functionality for configuring, initiating, monitoring and evaluating the FRM and QRM manoeuvres may reside in such a patient monitoring system, or an external computer connectable to the breathing apparatus or the patient monitoring system. Consequently, it should be realised that the above described OLT tool may reside partially or entirely within any of the breathing apparatus 2, an external patient monitoring system or an external computer.

Figure 9:
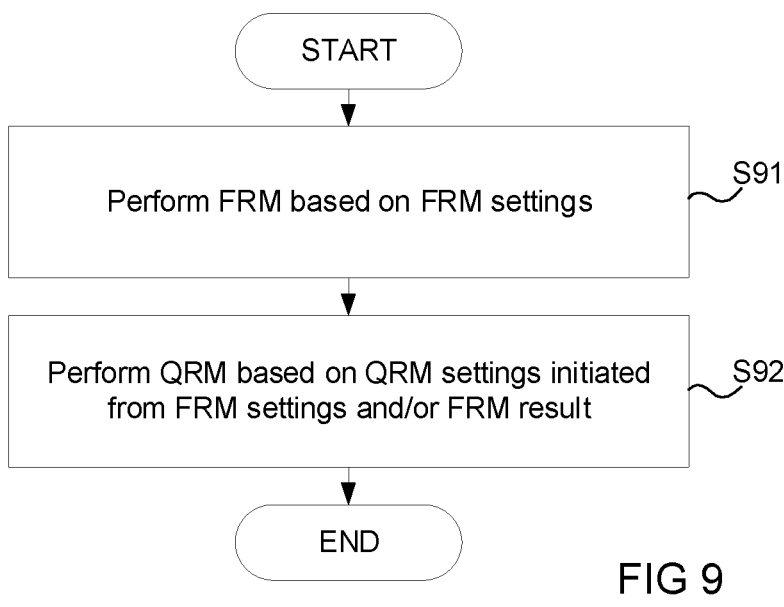
FIGS. 9 and 10 are flowcharts illustrating a method for lung recruitment in a mechanically ventilated patient, according to exemplary embodiments of the disclosure.

FIG. 9 illustrates a method for lung recruitment of a mechanically ventilated patient, according to an exemplary embodiment of the disclosure. With simultaneous reference made to previous drawings, the method is typically a computer-implemented method that is performed by the ventilation system 1 upon execution of a computer program by a computer of the ventilation system, such as the computer 15 of the breathing apparatus 2.

In a first step, S91, an FRM manoeuvre based on FRM settings is performed at a first point in time. The FRM manoeuvre comprises a recruitment phase and a PEEP titration phase.

In a second and final step, S92, a QRM manoeuvre based on QRM settings is performed for the same patient at a second and later point in time. The QRM manoeuvre comprises a recruitment phase but no PEEP titration phase. At least one QRM setting is initiated based on at least one FRM setting used for the FRM manoeuvre, and/or a result of the FRM manoeuvre.

Figure 10:
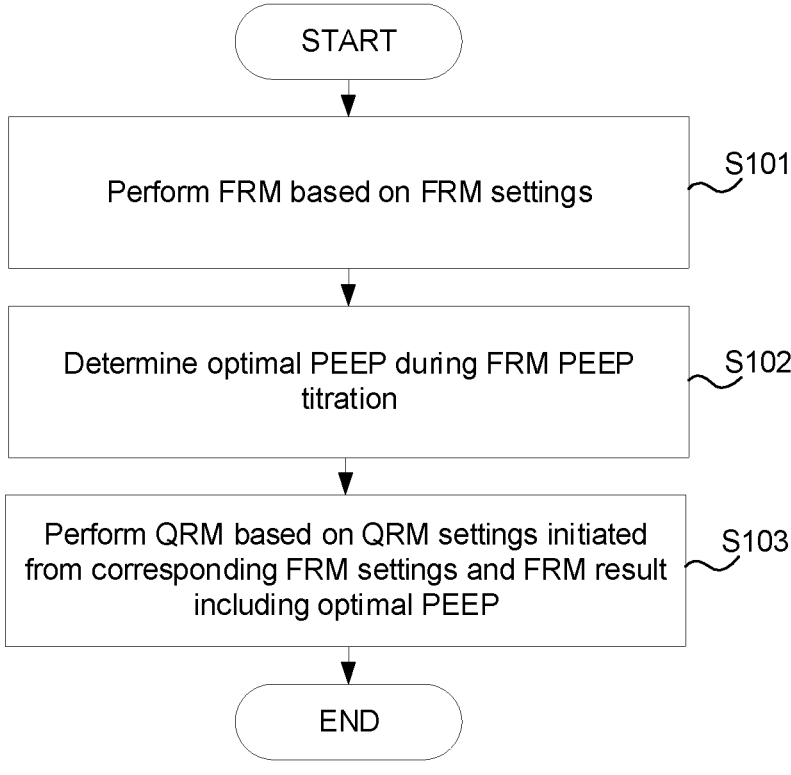

FIG. 10 illustrates an exemplary embodiment of a method for lung recruitment of a mechanically ventilated patient, where some QRM settings are initiated from corresponding FRM settings used for the FRM manoeuvre, whereas other QRM settings are initiated from results of the FRM manoeuvre, i.e. from parameters determined during the FRM manoeuvre.

In a first step, S101, an FRM manoeuvre based on FRM settings is performed at a first point in time. The FRM manoeuvre comprises a recruitment phase and a PEEP titration phase.

In a second step, S102, an optimal PEEP is determined during the PEEP titration phase of the FRM manoeuvre. As described above, the optimal PEEP may for instance be determined based on an identified closing PEEP substantially corresponding to the alveolar closing pressure of the ventilated patient.

In a third and final step, S103, a QRM manoeuvre based on QRM settings is performed for the same patient at a second and later point in time. The QRM manoeuvre comprises a recruitment phase but no PEEP titration phase. In this embodiment, the QRM settings are initiated in part from corresponding FRM setting used for the FRM manoeuvre and in part from a result of the FRM manoeuvre including the optimal PEEP determined in step S102. Preferably, most or all of the QRM settings defining the PEEP and PIP trajectories of the QRM recruitment staircase are initiated from corresponding FRM settings for defining the PEEP and PIP trajectories of the FRM recruitment staircase, whereas the QRM setting Post-RM PEEP for setting the PEEP following the QRM manoeuvre is initiated based on the optimal PEEP.

The invention claimed is:

1. A ventilation system, comprising:
a breathing apparatus for providing mechanical ventilation to a patient, the breathing apparatus being configured to perform, at a first point in time,
an automated full recruitment manoeuvre, FRM, comprising a recruitment phase, a PEEP titration phase, and a re-recruitment phase, the FRM being performed based on preset FRM settings, and, at a second and later point in time following a period of baseline ventilation,
an automated quick recruitment manoeuvre, QRM, comprising a recruitment phase but no PEEP titration phase or re-recruitment phase, the QRM being performed based on preset QRM settings, the breathing apparatus being configured to initiate at least one QRM setting based on a result of the FRM, wherein the at least one QRM setting comprises a PEEP max setting for setting a maximum PEEP for the recruitment phase of the QRM, in which the maximum PEEP setting is initiated from an optimal PEEP or an alveolar opening pressure of the patient determined during the FRM, and
wherein the breathing apparatus is configured to determine a time elapsed since the FRM was performed, and to initiate the at least one QRM setting from the result of the FRM only if the time elapsed is less than a predefined threshold value.

2. The ventilation system of claim 1, wherein the at least one QRM setting further comprises a maximum peak inspiratory pressure, PIP, setting to be used during the recruitment phase of the QRM, which maximum PIP setting is initiated from an optimal PEEP and/or an alveolar opening pressure of the patient, determined during the FRM.

3. The ventilation system of claim 1, wherein the breathing apparatus is configured to initiate the at least one QRM setting based on a corresponding FRM setting used for the FRM, and to initiate at least one other QRM setting based on the result of the FRM.

4. The ventilation system of claim 1, wherein the at least one QRM setting further comprises QRM recruitment settings defining a pressure trajectory for PIP (H) and a pressure trajectory for PEEP (I) to be followed during the recruitment phase of the QRM, which the QRM recruitment settings are initiated based on corresponding FRM settings defining a pressure trajectory for PIP (A) and a pressure trajectory for PEEP (B) used for the FRM.

5. The ventilation system of claim 1, wherein the breathing apparatus is configured to monitor at least one parameter being indicative of collapse of alveoli to initiate the at least one QRM setting from settings and/or results of the FRM based on a change of the parameter or if a predefined threshold value of the parameter is reached or to initiate the at least one QRM setting from settings and/or results of the FRM if a certain time has elapsed since the FRM last performed.

6. The ventilation system of claim 1, wherein the at least one QRM setting is any of, or any combination of:
a PIP max setting for setting a maximum PIP for the recruitment phase of the QRM, which the PIP max setting is initiated from any of, or any combination of, a corresponding PIP max setting set for the FRM, an alveolar opening pressure determined during the FRM, and an optimal PEEP determined during the FRM;
a PEEP incr/step setting for setting an incremental increase in PEEP between consecutive PEEP steps of the recruitment phase of the QRM, which the PEEP incr/step setting is initiated from a corresponding PEEP incr/step setting set for the FRM;

a recruitment rate setting for setting a respiratory rate for the recruitment phase of the QRM, which the recruitment rate setting is initiated from a corresponding recruitment rate setting set for the FRM;

a breaths/step setting for setting a number of breaths on each PEEP step of the recruitment phase of the QRM, which the breaths/step setting is initiated from a corresponding breaths/step setting set for the FRM;

a breaths at PEEP max setting for setting a number of breaths at the maximum PEEP level of the recruitment phase of the QRM, which the Breaths at PEEP max setting is initiated from a corresponding breaths at PEEP max setting set for the FRM; and a post-RM PEEP setting for setting a PEEP for a period of post-RM ventilation following the QRM.

7. A method for a lung recruitment in a mechanically ventilated patient, comprising the steps of:

performing, at a first point in time, an automated full recruitment manoeuvre, FRM, comprising a recruitment phase, a PEEP titration phase, and a re-recruitment phase, the FRM being performed based on preset FRM settings, and performing, at a second and later point in time following a period of baseline ventilation, an automated quick recruitment manoeuvre, QRM, comprising a recruitment phase but no PEEP titration phase or re-recruitment phase, the QRM being performed based on preset QRM settings, wherein at least one of the QRM settings is initiated based on a result of the FRM, wherein the at least one QRM setting comprises a PEEP max setting for setting a maximum PEEP for the recruitment phase of the QRM, in which the maximum PEEP setting is initiated from an optimal PEEP or an alveolar opening pressure of the patient determined during the FRM, and wherein the breathing apparatus is configured to determine a time elapsed since the FRM was performed, and to initiate the at least one QRM setting from the result of the FRM only if the time elapsed is less than a predefined threshold value.

8. The method of claim 7, wherein the at least one QRM setting further comprises a maximum PIP setting to be used during the recruitment phase of the QRM, which maximum PIP setting is initiated from an optimal PEEP and/or an alveolar opening pressure of the patient, determined during the FRM.

9. The method of claim 7, wherein the at least one QRM setting is initiated based on a corresponding FRM setting used for the FRM, and at least one other QRM setting is initiated based on the result of the FRM.

10. The method of claim 7, wherein the at least one QRM setting further comprises QRM recruitment settings defining a pressure trajectory for PIP (H) and a pressure trajectory for PEEP (I) to be followed during the QRM recruitment phase, which the QRM recruitment settings are initiated based on corresponding FRM settings defining a pressure trajectory for PIP (A) and a pressure trajectory for PEEP (B) used for the FRM.

11. A computer program for a lung recruitment in a mechanically ventilated patient, the computer program comprises computer-readable instruction which, when executed by a computer of a ventilation system comprising a breathing apparatus, causes the ventilation system to perform the method of claim 6.

*    *    *    *    *